(12) United States Patent
Tian et al.

(10) Patent No.: US 9,375,507 B2
(45) Date of Patent: *Jun. 28, 2016

(54) PARTICULATE SUPERABSORBENT POLYMER COMPOSITION HAVING IMPROVED STABILITY

(71) Applicant: Evonik Corporation, Parsippany, NJ (US)

(72) Inventors: Gonglu Tian, Henrico, VA (US); Matthew Thomas Ondisco, Greensboro, NC (US); David L. Bergman, Greensboro, NC (US); Bernfried Messner, Summerfield, NC (US); Scott J. Smith, Dusseldorf (DE); Mark Joy, Reidsville, NC (US)

(73) Assignee: Evonik Corporation, Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/157,769

(22) Filed: Jan. 17, 2014

(65) Prior Publication Data

US 2014/0306156 A1    Oct. 16, 2014

Related U.S. Application Data

(63) Continuation-in-part of application No. 13/860,019, filed on Apr. 10, 2013.

(51) Int. Cl.
| | | |
|---|---|---|
| B01J 20/32 | (2006.01) |
| B01J 20/26 | (2006.01) |
| A61L 15/60 | (2006.01) |
| C08J 3/12 | (2006.01) |
| C08J 3/24 | (2006.01) |
| C08F 220/06 | (2006.01) |
| A61L 15/42 | (2006.01) |
| B01J 20/00 | (2006.01) |
| A61L 15/18 | (2006.01) |
| A61L 15/00 | (2006.01) |
| C08L 33/00 | (2006.01) |

(52) U.S. Cl.
CPC .......... *A61L 15/60* (2013.01); *A61L 15/42* (2013.01); *C08F 220/06* (2013.01); *C08J 3/12* (2013.01); *C08J 3/126* (2013.01); *C08J 3/24* (2013.01); *A61L 15/00* (2013.01); *A61L 15/18* (2013.01); *A61L 2300/102* (2013.01); *B01J 20/00* (2013.01); *B01J 20/265* (2013.01); *B01J 20/3208* (2013.01); *B01J 20/3234* (2013.01); *B01J 20/3236* (2013.01); *B01J 2220/68* (2013.01); *C08L 33/00* (2013.01)

(58) Field of Classification Search
None
See application file for complete search history.

(56) References Cited

U.S. PATENT DOCUMENTS

| 4,340,556 A | 7/1982 | Ciencewicki |
| 4,392,908 A | 7/1983 | Dehnel |
| 4,540,454 A | 9/1985 | Iskra et al. |
| 4,559,050 A | 12/1985 | Iskra |
| 4,605,402 A | 8/1986 | Iskra |
| 4,676,784 A | 6/1987 | Erdman et al. |
| 4,927,346 A | 5/1990 | Kaiser et al. |
| 4,957,984 A | 9/1990 | Itoh et al. |
| 5,017,324 A | 5/1991 | Kaiser et al. |
| 5,041,464 A | 8/1991 | Hoshino et al. |
| 5,061,259 A | 10/1991 | Goldman et al. |
| 5,086,133 A | 2/1992 | Itoh et al. |
| 5,098,423 A | 3/1992 | Pieniak et al. |
| 5,100,397 A | 3/1992 | Poccia et al. |
| 5,143,680 A | 9/1992 | Molnar et al. |
| 5,154,754 A | 10/1992 | Damo et al. |
| 5,195,999 A | 3/1993 | Harada et al. |
| 5,216,044 A | 6/1993 | Hoshino et al. |
| 5,244,735 A | 9/1993 | Kimura et al. |

(Continued)

FOREIGN PATENT DOCUMENTS

| CA | 2460152 | 10/2009 |
| CN | 02819951 | 8/2007 |

(Continued)

OTHER PUBLICATIONS

Buchholz, Frederick L. and Graham, Andrew T., "Modern Superabsorbent Polymer Technology," copyright 1998, John Wiley & Sons, Inc., Chapter 1: "Absorbency and Superabsorbency," pp. 1-17 (19 pages).

(Continued)

*Primary Examiner* — Tanisha Diggs
(74) *Attorney, Agent, or Firm* — Bernard Lau; Linda S. Li; Jason S. Ngui

(57) ABSTRACT

The present invention relates to a particulate superabsorbent polymer composition comprising a polymer comprising a neutralized aluminum salt solution applied to the surface of a particulate superabsorbent polymer; wherein an aqueous solution of the neutralized aluminum salt has a pH value from about 5.5 to about 8 and the particulate superabsorbent polymer composition has a mean particle size distribution of from 300 to 400 μm, an original Free Swell Gel Bed Permeability (FSGBP) of about $20 \times 10^{-8}$ cm$^2$ to about $200 \times 10^{-8}$ cm$^2$; and subsequent to subjecting the particulate superabsorbent polymer composition to the Processing Test, the particulate superabsorbent polymer composition has a permeability stability index of from about 0.60 to about 0.99 and having particles having a particle diameter of larger than 600 μm in an amount of less than about 15 wt % of the particulate superabsorbent polymer composition and as specified by standard sieve classification.

21 Claims, 4 Drawing Sheets

(56) References Cited

U.S. PATENT DOCUMENTS

| | | |
|---|---|---|
| 5,273,824 A | 12/1993 | Hoshino et al. |
| 5,280,079 A | 1/1994 | Allen et al. |
| 5,369,148 A | 11/1994 | Takahashi et al. |
| 5,380,808 A | 1/1995 | Sumiya et al. |
| 5,409,771 A | 4/1995 | Dahmen et al. |
| 5,429,590 A | 7/1995 | Saito et al. |
| 5,451,613 A | 9/1995 | Smith et al. |
| 5,462,972 A | 10/1995 | Smith et al. |
| 5,473,023 A | 12/1995 | Mizukami et al. |
| 5,486,569 A | 1/1996 | Henderson et al. |
| 5,505,719 A | 4/1996 | Cohen et al. |
| 5,506,324 A | 4/1996 | Gartner et al. |
| 5,514,754 A | 5/1996 | Henderson et al. |
| 5,538,728 A | 7/1996 | Yanaki et al. |
| 5,559,263 A | 9/1996 | Smith |
| 5,569,226 A | 10/1996 | Cohen et al. |
| 5,629,377 A | 5/1997 | Burgert et al. |
| 5,684,106 A | 11/1997 | Johnson et al. |
| 5,720,736 A | 2/1998 | Hatsuda et al. |
| 5,728,083 A | 3/1998 | Cohen et al. |
| 5,763,331 A | 6/1998 | Demhartner |
| 5,766,388 A | 6/1998 | Pelley et al. |
| 5,830,543 A | 11/1998 | Miyake et al. |
| 5,837,789 A | 11/1998 | Stockhausen et al. |
| 5,853,867 A | 12/1998 | Harada et al. |
| 5,961,506 A | 10/1999 | Guidotti et al. |
| 5,976,696 A | 11/1999 | Collette et al. |
| 5,981,689 A | 11/1999 | Mitchell et al. |
| 5,985,944 A | 11/1999 | Ishizaki et al. |
| 5,994,419 A | 11/1999 | Collette et al. |
| 5,994,440 A | 11/1999 | Staples et al. |
| 5,997,791 A | 12/1999 | Chou et al. |
| 6,037,518 A | 3/2000 | Guidotti et al. |
| 6,068,619 A | 5/2000 | Hamajima et al. |
| 6,072,101 A | 6/2000 | Beihoffer et al. |
| 6,087,450 A | 7/2000 | Breitbach et al. |
| 6,090,875 A | 7/2000 | Staples et al. |
| 6,121,409 A | 9/2000 | Mitchell et al. |
| 6,124,391 A | 9/2000 | Sun et al. |
| 6,143,821 A | 11/2000 | Houben |
| 6,156,678 A | 12/2000 | Mukaida et al. |
| 6,159,591 A | 12/2000 | Beihoffer et al. |
| 6,162,541 A | 12/2000 | Chou et al. |
| 6,194,631 B1 | 2/2001 | Mitchell et al. |
| 6,222,091 B1 | 4/2001 | Beihoffer et al. |
| 6,229,062 B1 | 5/2001 | Mandell et al. |
| 6,235,965 B1 | 5/2001 | Beihoffer et al. |
| 6,251,960 B1 | 6/2001 | Ishizaki et al. |
| 6,265,488 B1 | 7/2001 | Nagasuna et al. |
| 6,290,813 B1 | 9/2001 | Woodrum |
| 6,294,588 B1 | 9/2001 | Chou et al. |
| 6,300,275 B1 | 10/2001 | Weir |
| 6,313,231 B1 | 11/2001 | Hosokawa et al. |
| 6,342,298 B1 | 1/2002 | Evans et al. |
| 6,348,133 B1 | 2/2002 | Woodrum et al. |
| 6,359,049 B1 | 3/2002 | Carrico et al. |
| 6,376,072 B1 | 4/2002 | Evans et al. |
| 6,392,116 B1 | 5/2002 | Beihoffer et al. |
| 6,399,668 B1 | 6/2002 | Miyake et al. |
| 6,414,214 B1 | 7/2002 | Engelhardt et al. |
| 6,429,265 B2 | 8/2002 | Nishida |
| 6,441,268 B1 | 8/2002 | Edwardsson |
| 6,458,877 B1 | 10/2002 | Ahmed et al. |
| 6,465,379 B1 | 10/2002 | Cook et al. |
| 6,465,536 B2 | 10/2002 | Chou et al. |
| 6,509,512 B1 | 1/2003 | Beihoffer et al. |
| 6,514,615 B1 | 2/2003 | Sun et al. |
| 6,534,572 B1 | 3/2003 | Ahmed et al. |
| 6,555,502 B1 | 4/2003 | Beihoffer et al. |
| 6,559,081 B1 | 5/2003 | Erspamer et al. |
| 6,562,742 B2 | 5/2003 | Dutkiewicz et al. |
| 6,562,743 B1 | 5/2003 | Cook et al. |
| 6,565,981 B1 | 5/2003 | Messner et al. |
| 6,569,137 B2 | 5/2003 | Suzuki et al. |
| 6,573,422 B1 | 6/2003 | Rosenfeld et al. |
| 6,590,137 B2 | 7/2003 | Mitchell et al. |
| 6,592,960 B1 | 7/2003 | Suzuki et al. |
| 6,596,921 B2 | 7/2003 | Beihoffer et al. |
| 6,596,922 B2 | 7/2003 | Beihoffer et al. |
| 6,603,055 B2 | 8/2003 | Mitchell et al. |
| 6,603,056 B2 | 8/2003 | Beihoffer et al. |
| 6,620,889 B2 | 9/2003 | Mertens et al. |
| 6,623,576 B2 | 9/2003 | Mitchell et al. |
| 6,649,810 B1 | 11/2003 | Minato et al. |
| 6,667,424 B1 | 12/2003 | Hamilton et al. |
| 6,743,391 B2 | 6/2004 | Sun et al. |
| 6,770,576 B2 | 8/2004 | Cook et al. |
| 6,790,798 B1 | 9/2004 | Suzuki et al. |
| 6,831,142 B2 | 12/2004 | Mertens et al. |
| 6,841,229 B2 | 1/2005 | Sun et al. |
| 6,849,665 B2 | 2/2005 | Frenz et al. |
| 6,849,672 B2 | 2/2005 | Mehawej et al. |
| 6,891,080 B2 | 5/2005 | Minato et al. |
| 6,905,986 B2 | 6/2005 | Ranganathan et al. |
| 6,906,131 B2 | 6/2005 | Ahmed et al. |
| 6,951,911 B2 | 10/2005 | Tagawa et al. |
| 6,998,367 B2 | 2/2006 | Qin |
| 7,087,669 B2 | 8/2006 | Ota et al. |
| 7,157,141 B2 | 1/2007 | Inger et al. |
| 7,163,966 B2 | 1/2007 | Joy et al. |
| 7,163,969 B2 | 1/2007 | Ahmed et al. |
| 7,163,992 B2 | 1/2007 | Kaai |
| 7,169,843 B2 | 1/2007 | Smith et al. |
| 7,173,086 B2 | 2/2007 | Smith et al. |
| 7,176,149 B2 | 2/2007 | Dutkiewicz et al. |
| 7,179,851 B2 | 2/2007 | Qin et al. |
| 7,179,862 B2 | 2/2007 | Mertens et al. |
| 7,183,456 B2 | 2/2007 | Hatsuda et al. |
| 7,241,820 B2 | 7/2007 | Smith et al. |
| 7,282,262 B2 | 10/2007 | Adachi et al. |
| 7,285,599 B2 | 10/2007 | Mertens et al. |
| 7,285,614 B2 | 10/2007 | Jonas et al. |
| 7,285,615 B2 | 10/2007 | Adachi et al. |
| 7,291,674 B2 | 11/2007 | Kang et al. |
| 7,312,278 B2 | 12/2007 | Nakashima et al. |
| 7,312,286 B2 | 12/2007 | Lang et al. |
| 7,329,701 B2 | 2/2008 | Herfert et al. |
| 7,335,713 B2 | 2/2008 | Lang et al. |
| 7,344,522 B2 | 3/2008 | Suzuki et al. |
| 7,361,712 B2 | 4/2008 | Satake et al. |
| 7,396,584 B2 | 7/2008 | Azad et al. |
| 7,399,813 B2 | 7/2008 | Lang et al. |
| 7,427,650 B2 | 9/2008 | Smith et al. |
| 7,435,477 B2 | 10/2008 | Adachi et al. |
| 7,462,754 B2 | 12/2008 | Malowaniec et al. |
| 7,473,470 B2 | 1/2009 | Ishizaki et al. |
| 7,473,739 B2 | 1/2009 | Dairoku et al. |
| 7,482,058 B2 | 1/2009 | Ahmed et al. |
| 7,488,541 B2 | 2/2009 | Ahmed et al. |
| 7,507,475 B2 | 3/2009 | Inger et al. |
| 7,510,988 B2 | 3/2009 | Wada et al. |
| 7,521,109 B2 | 4/2009 | Suzuki et al. |
| 7,553,903 B2 | 6/2009 | Riegel et al. |
| 7,572,864 B2 | 8/2009 | Mertens et al. |
| 7,579,402 B2 | 8/2009 | Ahmed et al. |
| 7,582,705 B2 | 9/2009 | Dairoku et al. |
| 7,608,748 B2 | 10/2009 | Zoch et al. |
| 7,615,579 B2 | 11/2009 | Joy et al. |
| 7,638,570 B2 | 12/2009 | Torii et al. |
| 7,642,207 B2 | 1/2010 | Boehmer et al. |
| 7,662,460 B2 | 2/2010 | Herfert et al. |
| 7,662,745 B2 | 2/2010 | Zhang et al. |
| 7,663,016 B2 | 2/2010 | Suzuki |
| 7,732,050 B2 | 6/2010 | Nambu et al. |
| 7,737,224 B2 | 6/2010 | Willis et al. |
| 7,745,537 B2 | 6/2010 | Nakashima et al. |
| 7,777,093 B2 | 8/2010 | Smith et al. |
| 7,786,182 B2 | 8/2010 | Iwamura et al. |
| 7,790,823 B2 | 9/2010 | Funk et al. |
| 7,795,345 B2 | 9/2010 | Smith et al. |
| 7,803,880 B2 | 9/2010 | Torii et al. |
| 7,812,082 B2 | 10/2010 | McIntosh et al. |
| 7,816,426 B2 | 10/2010 | Ahmed et al. |
| 7,838,610 B2 | 11/2010 | Adachi |

(56) References Cited

U.S. PATENT DOCUMENTS

| | | |
|---|---|---|
| 7,842,386 B2 | 11/2010 | Loeker et al. |
| 7,850,672 B2 | 12/2010 | Guidotti et al. |
| 7,855,315 B2 | 12/2010 | Mitchell et al. |
| 7,867,623 B2 | 1/2011 | Ziemer et al. |
| 7,872,076 B2 | 1/2011 | Ikeuchi et al. |
| 7,888,548 B2 | 2/2011 | Guidotti |
| 7,906,585 B2 | 3/2011 | McIntosh et al. |
| 7,910,688 B2 | 3/2011 | Tian et al. |
| 7,915,363 B2 | 3/2011 | Funk et al. |
| 7,919,564 B2 | 4/2011 | Shibata et al. |
| 7,919,565 B2 | 4/2011 | Willis et al. |
| 7,935,774 B2 | 5/2011 | Ikeuchi et al. |
| 7,960,469 B2 | 6/2011 | Adachi et al. |
| 7,976,523 B2 | 7/2011 | Suzuki et al. |
| 7,981,833 B2 | 7/2011 | Ikeuchi et al. |
| 7,981,969 B2 | 7/2011 | Riegel et al. |
| 7,981,970 B2 | 7/2011 | Willis et al. |
| 7,994,233 B2 | 8/2011 | Mehawej et al. |
| 8,003,733 B2 | 8/2011 | Willis et al. |
| 8,017,549 B2 | 9/2011 | Herfert et al. |
| 8,021,998 B2 | 9/2011 | Qin et al. |
| 8,026,294 B2 | 9/2011 | Wada et al. |
| 8,058,353 B2 | 11/2011 | Willis et al. |
| 8,058,370 B2 | 11/2011 | Hibino et al. |
| 8,063,118 B2 | 11/2011 | Ahmed et al. |
| 8,063,265 B2 | 11/2011 | Beck et al. |
| 8,071,222 B2 | 12/2011 | Ziemer et al. |
| 8,084,546 B2 | 12/2011 | Willis et al. |
| 8,198,209 B2 | 6/2012 | Torii et al. |
| 8,198,385 B2 | 6/2012 | Gartner et al. |
| 8,222,477 B2 | 7/2012 | Azad et al. |
| 8,236,876 B2 | 8/2012 | Ahmed et al. |
| 8,236,884 B2 | 8/2012 | Smith et al. |
| 8,247,491 B2 | 8/2012 | Torii et al. |
| 8,252,873 B1 | 8/2012 | Gartner et al. |
| 8,257,610 B2 | 9/2012 | Torii et al. |
| 8,258,223 B2 | 9/2012 | Riegel et al. |
| 8,268,424 B1 | 9/2012 | Suzuki et al. |
| 8,288,002 B2 | 10/2012 | Loeker et al. |
| 8,288,491 B2 | 10/2012 | Gotou et al. |
| 8,304,369 B2 | 11/2012 | Tian et al. |
| 8,309,682 B2 | 11/2012 | Tian et al. |
| 8,318,306 B2 | 11/2012 | Tian et al. |
| 8,318,895 B1 | 11/2012 | Tian et al. |
| 8,361,926 B2 | 1/2013 | Tian et al. |
| 8,378,033 B2 | 2/2013 | Handa et al. |
| 8,383,746 B2 | 2/2013 | Torii et al. |
| 8,403,904 B2 | 3/2013 | Tian et al. |
| 8,426,670 B2 | 4/2013 | Nagasuna et al. |
| 8,481,664 B2 | 7/2013 | Dairoku et al. |
| 8,487,049 B2 | 7/2013 | Tian et al. |
| 8,507,620 B2 | 8/2013 | Kim et al. |
| 8,518,541 B2 | 8/2013 | Loeker et al. |
| 8,647,317 B2 | 2/2014 | Tian et al. |
| 8,648,161 B2 | 2/2014 | Fujino et al. |
| 8,734,948 B2 | 5/2014 | Tian et al. |
| 8,802,786 B2 | 8/2014 | Shi et al. |
| 8,865,828 B2 | 10/2014 | Daniel et al. |
| 2002/0013560 A1 | 1/2002 | Erspamer et al. |
| 2003/0065296 A1 | 4/2003 | Kaiser et al. |
| 2003/0100873 A1 | 5/2003 | Hermansson et al. |
| 2003/0139716 A1 | 7/2003 | Falk |
| 2003/0144379 A1 | 7/2003 | Mitchell et al. |
| 2003/0149413 A1 | 8/2003 | Mehawej |
| 2003/0181115 A1 | 9/2003 | Nagasuna et al. |
| 2003/0208175 A1 | 11/2003 | Gross et al. |
| 2003/0219573 A1 | 11/2003 | Falk |
| 2004/0019342 A1 | 1/2004 | Nagasuna et al. |
| 2004/0081829 A1 | 4/2004 | Klier et al. |
| 2005/0031850 A1 | 2/2005 | Rausch et al. |
| 2005/0096435 A1 | 5/2005 | Smith et al. |
| 2005/0153615 A1 | 7/2005 | Dutkiewicz et al. |
| 2005/0234413 A1 | 10/2005 | Funk et al. |
| 2006/0167424 A1 | 7/2006 | Chang et al. |
| 2006/0282052 A1 | 12/2006 | Saito et al. |
| 2007/0129495 A1 | 6/2007 | Mertens et al. |
| 2007/0135554 A1 | 6/2007 | McIntosh et al. |
| 2007/0152365 A1 | 7/2007 | Dutkiewicz et al. |
| 2008/0009616 A1 | 1/2008 | Frank et al. |
| 2008/0032888 A1 | 2/2008 | Nakamura et al. |
| 2008/0147029 A1 | 6/2008 | Pate et al. |
| 2008/0234420 A1 | 9/2008 | Smith et al. |
| 2008/0281049 A1 | 11/2008 | Wendker et al. |
| 2009/0012486 A1 | 1/2009 | Riegel et al. |
| 2009/0018517 A1 | 1/2009 | Cecconi et al. |
| 2009/0062760 A1 | 3/2009 | Wright et al. |
| 2009/0105389 A1 | 4/2009 | Walden et al. |
| 2009/0134357 A1 | 5/2009 | Bub et al. |
| 2009/0177174 A1 | 7/2009 | Akiyama et al. |
| 2009/0204087 A1 | 8/2009 | Herfert et al. |
| 2009/0306290 A1 | 12/2009 | Bucevschi et al. |
| 2009/0326497 A1 | 12/2009 | Schmidt |
| 2010/0010461 A1 | 1/2010 | Herfert et al. |
| 2010/0062165 A1 | 3/2010 | Suzuki et al. |
| 2010/0062934 A1 | 3/2010 | Suzuki et al. |
| 2010/0063469 A1 | 3/2010 | Herfert |
| 2010/0063470 A1 | 3/2010 | Suzuki et al. |
| 2010/0069592 A1 | 3/2010 | Matzuaki et al. |
| 2010/0075844 A1 | 3/2010 | Loeker et al. |
| 2010/0100065 A1 | 4/2010 | De Angelis et al. |
| 2010/0137773 A1 | 6/2010 | Gross et al. |
| 2010/0204403 A1 | 8/2010 | Willis et al. |
| 2010/0206897 A1 | 8/2010 | Herfert et al. |
| 2010/0247916 A1 | 9/2010 | Hamilton et al. |
| 2010/0261799 A1 | 10/2010 | Vachon et al. |
| 2010/0273647 A1 | 10/2010 | Nawata et al. |
| 2010/0279860 A1 | 11/2010 | Smith et al. |
| 2010/0298514 A1 | 11/2010 | Willis et al. |
| 2010/0308263 A1 | 12/2010 | Torii et al. |
| 2010/0311578 A1 | 12/2010 | Smith et al. |
| 2010/0326580 A1 | 12/2010 | Mori et al. |
| 2011/0015362 A1 | 1/2011 | Possemiers et al. |
| 2011/0021712 A1 | 1/2011 | Gotou et al. |
| 2011/0040060 A1 | 2/2011 | Gotou et al. |
| 2011/0059329 A1 | 3/2011 | Dobrawa et al. |
| 2011/0118430 A1 | 5/2011 | Funk et al. |
| 2011/0125119 A1 | 5/2011 | Weismantel et al. |
| 2011/0130275 A1 | 6/2011 | Weismantel et al. |
| 2011/0130735 A1 | 6/2011 | Weismantel et al. |
| 2011/0238026 A1 | 9/2011 | Zhang et al. |
| 2011/0257340 A1 | 10/2011 | Herfert et al. |
| 2011/0275513 A1 | 11/2011 | Tian et al. |
| 2011/0281977 A1 | 11/2011 | Edvardsson et al. |
| 2011/0301560 A1 | 12/2011 | Fujimura et al. |
| 2011/0306732 A1 | 12/2011 | Fujino et al. |
| 2012/0010372 A1 | 1/2012 | Fujino et al. |
| 2012/0035294 A1 | 2/2012 | Kim et al. |
| 2012/0045639 A1 | 2/2012 | Whitmore et al. |
| 2012/0085971 A1 | 4/2012 | Daniel et al. |
| 2012/0108421 A1 | 5/2012 | Akiyama et al. |
| 2012/0109091 A1 | 5/2012 | Akiyama et al. |
| 2012/0184670 A1 | 7/2012 | Kobayashi et al. |
| 2012/0202959 A1 | 8/2012 | Herfert et al. |
| 2012/0211699 A1 | 8/2012 | Daniel et al. |
| 2012/0220452 A1 | 8/2012 | Matsumoto et al. |
| 2012/0267570 A1 | 10/2012 | Shi et al. |
| 2012/0271260 A1 | 10/2012 | Azad et al. |
| 2012/0277096 A1 | 11/2012 | Smith et al. |
| 2012/0298913 A1 | 11/2012 | Kondo et al. |
| 2013/0040811 A1 | 2/2013 | Tian et al. |
| 2013/0079221 A1 | 3/2013 | Tian et al. |
| 2013/0096000 A1 | 4/2013 | Tian et al. |
| 2013/0175472 A1 | 7/2013 | Tian et al. |
| 2013/0277608 A1 | 10/2013 | Tian et al. |
| 2013/0310251 A1 | 11/2013 | Smith et al. |
| 2014/0306155 A1 | 10/2014 | Tian et al. |
| 2014/0306156 A1 | 10/2014 | Tian et al. |
| 2014/0316040 A1 | 10/2014 | Shi et al. |

FOREIGN PATENT DOCUMENTS

| | | |
|---|---|---|
| CN | 102300884 A | 12/2011 |
| CN | 102906135 A | 1/2013 |
| EP | 1169372 A1 | 1/2002 |

(56) References Cited

FOREIGN PATENT DOCUMENTS

| | | |
|---|---|---|
| EP | 1315528 A1 | 6/2003 |
| EP | 1315770 A1 | 6/2003 |
| EP | 1438354 A1 | 7/2004 |
| EP | 1765913 A1 | 3/2007 |
| EP | 2395029 A1 | 12/2011 |
| EP | 2399944 A1 | 12/2011 |
| EP | 2518092 A1 | 10/2012 |
| EP | 2566901 A1 | 3/2013 |
| JP | 2013525592 A | 6/2013 |
| TW | 201304825 A | 2/2013 |
| TW | 201504314 A | 2/2015 |
| TW | 201504315 A | 2/2015 |
| WO | 0053664 A1 | 9/2000 |
| WO | 0220068 A1 | 3/2002 |
| WO | 0222717 A1 | 3/2002 |
| WO | 03025054 A1 | 3/2003 |
| WO | 2004096304 A1 | 11/2004 |
| WO | 2005108472 A1 | 11/2005 |
| WO | 2006109844 A1 | 10/2006 |
| WO | 2010057912 A1 | 5/2010 |
| WO | 2010108875 A1 | 9/2010 |
| WO | 2011117187 A1 | 9/2011 |
| WO | 2011139883 A1 | 11/2011 |
| WO | 2012107432 A1 | 8/2012 |
| WO | 2012143215 A1 | 10/2012 |

OTHER PUBLICATIONS

Buchholz, Frederick L. and Graham, Andrew T., "Modern Superabsorbent Polymer Technology," copyright 1998, John Wiley & Sons, Inc., Chapter 2: "Chemistry of Superabsorbent Polyacrylates," pp. 19-67 (51 pages).

Buchholz, Frederick L. and Graham, Andrew T., "Modern Superabsorbent Polymer Technology," copyright 1998, John Wiley & Sons, Inc., Chapter 3: "Commercial Processes for the Manufacture of Superabsorbent Polymers," pp. 69-117 (51 pages).

Buchholz, Frederick L. and Graham, Andrew T., "Modern Superabsorbent Polymer Technology," copyright 1998, John Wiley & Sons, Inc., Chapter 4: "Analysis and Characterization of Superabsorbent Polymers," pp. 119-165 (49 pages).

Buchholz, Frederick L. and Graham, Andrew T., "Modern Superabsorbent Polymer Technology," copyright 1998, John Wiley & Sons, Inc., Chapter 5: "The Structure and Properties of Superabsorbent Polyacrylates," pp. 167-221 (57 pages).

International Search Report mailed on Jul. 4, 2012 in PCT/EP2012/055472 (3 pages).

Smith et al., U.S. Appl. No. 13/953,844, filed Jul. 30, 2013.

Written Opinion mailed on Jul. 4, 2012 in PCT/EP2012/055472 (4 pages).

International Search Report mailed on Jun. 26, 2014 in PCT/US2014/033142 (4 pages).

Written Opinion mailed on Jun. 26, 2014 in PCT/US2014/033142 (6 pages).

International Search Report mailed on May 15, 2014 in PCT/EP2014/057221 (3 pages).

Written Opinion mailed on May 15, 2014 in PCT/EP2014/057221 (5 pages).

Taiwan Search Report mailed on Apr. 10, 2015 in Taiwan Application No. 103112937 (1 page).

PARTICULATE SUPERABSORBENT POLYMER COMPOSITION HAVING IMPROVED STABILITY

FIELD OF THE INVENTION

The present invention relates to particulate superabsorbent polymer compositions which absorb water, aqueous liquids, and blood, and a method to make the particulate superabsorbent polymer compositions. In particular, the present invention relates to particulate superabsorbent polymer compositions having high permeability and improved stability of the particulate superabsorbent polymer compositions after processing. This invention is also directed to improving the stability of the properties of the particulate superabsorbent polymer compositions including permeability.

BACKGROUND OF THE INVENTION

A superabsorbent polymer, in general refers to a water-swellable, water-insoluble polymer, or material, capable of absorbing at least about 10 times its weight, and up to about 30 times or more its weight in an aqueous solution containing 0.9 weight percent sodium chloride solution in water. Examples of superabsorbent polymer may include a crosslinked partially neutralized acrylate polymer, and the formation of superabsorbent hydrogel from the polymerization, and formation of particulate superabsorbent polymer compositions capable of retaining the aqueous liquids under a certain pressure in accordance with the general definition of superabsorbent polymer.

The superabsorbent polymer hydrogel can be formed into particles, generally referred to as particulate superabsorbent polymer, wherein the particulate superabsorbent polymer may be surface-treated with surface crosslinking, and other surface treatment and post treated after surface crosslinking to form particulate superabsorbent polymer compositions. The acronym SAP may be used in place of superabsorbent polymer, superabsorbent polymer composition, particulate superabsorbent polymer compositions, or variations thereof. Commercial particulate superabsorbent polymer compositions are widely used in a variety of personal care products, such as infant diapers, child training pants, adult incontinence products, feminine care products, and the like. In general, these particulate superabsorbent polymer compositions have a centrifuge retention capacity (CRC) of at least 25 grams of 0.9 weight percent sodium chloride aqueous solution per gram of the polymer. Particulate superabsorbent polymer compositions are also designed to quickly uptake bodily fluids, which require high gel bed permeability (GBP). Commercial particulate superabsorbent polymer compositions undergo significant processing during manufacturing and converting processes, resulting in lack of stability of the original gel bed permeability. This lack of stability or reduction of the value of various properties, including gel bed permeability may be one of the causes of premature leakage and skin wetness problems for absorbent articles.

There is thus a need or desire for particulate superabsorbent polymer compositions that can withstand absorbent product manufacturing and converting processes without resulting in a significant reduction in properties. There is a further need or desire for a method of increasing the permeability stability of a particulate superabsorbent polymer composition.

SUMMARY OF THE INVENTION

The present invention is directed to a particulate superabsorbent polymer composition having improved stability comprising a particulate superabsorbent polymer and from 0.01 wt % to about 5 wt % based on the particulate superabsorbent polymer composition weight of a neutralized aluminum salt applied to the surface of the particulate superabsorbent polymer, in the form of an aqueous neutralized aluminum salt solution having a pH value from about 5.5 to about 8; wherein the particulate superabsorbent polymer composition has a centrifuge retention capacity of from about 25 grams to about 40 grams of 0.9 weight percent sodium chloride aqueous per gram of the particulate superabsorbent polymer composition and an original Free Swell Gel Bed Permeability (FSGBP) of about $20\times10^{-8}$ $cm^2$ to about $200\times10^{-8}$ $cm^2$ prior to subjecting the particulate superabsorbent polymer composition to a Processing Test; and a compressibility of from about 1.30 $mm^2/N$ to about 4 $mm^2/N$ and having particles having a particle diameter of larger than 600 µm in an amount of less than about 15 wt % of the particulate superabsorbent polymer composition and as specified by standard sieve classification.

In addition, the present invention is directed to a particulate superabsorbent polymer composition having improved stability comprising a particulate superabsorbent polymer and from 0.01 wt % to about 5 wt % based on the particulate superabsorbent polymer composition weight of a neutralized aluminum salt applied to the surface of the particulate superabsorbent polymer, in the form of an aqueous neutralized aluminum salt solution having a pH value from about 5.5 to about 8; wherein said particulate superabsorbent polymer composition has particles having a particle diameters of smaller than 600 µm and larger than 150 µm in an amount of not less than about 85 wt % of the particulate superabsorbent polymer composition and as specified by standard sieve classification and the particles having a weight average particle diameter (D50) specified by standard sieve classification of from 300 to 400 µm.

In addition, the present invention is directed to a particulate superabsorbent polymer composition having improved stability comprising:

a) from about 55 wt % to about 85 wt % of polymerizable unsaturated acid group containing monomers selected from acrylic acid, methacrylic acid, or 2-acrylamido-2-methylpropanesulfonic acid, or mixtures thereof;

b) from about 14 wt % to about 45 wt % of an alkali base selected from sodium hydroxide or potassium hydroxide to neutralize the polymerizable unsaturated acid group containing monomers of a) to from about 50 to about 80 mol %;

c) from about 0.001 wt % to about 5.0 wt % based on the weight of a) of an internal crosslinking agent, wherein the components a), b) and c) are polymerized into a hydrogel which is granulated into particulate superabsorbent polymer having a surface;

d) from about 0.001 wt % to about 5.0 wt % based on the particulate superabsorbent composition weight of surface crosslinking agent applied to the surface of the particulate superabsorbent polymer;

e) from 0.001 wt to about 5.0 wt % based on the particulate superabsorbent composition weight of a neutralized aluminum salt applied to the surface of the particulate superabsorbent polymer, in the form of an aqueous neutralized aluminum salt solution having a pH value from about 5.5 to about 8;

wherein the particulate superabsorbent polymer composition has a centrifuge retention capacity of from about 25 grams to about 40 grams of 0.9 weight percent sodium chloride aqueous per gram of the particulate superabsorbent polymer composition and an original Free Swell Gel Bed Permeability (FSGBP) of about $20\times10^{-8}$ $cm^2$ to about $200\times10^{-8}$ $cm^2$ prior to subjecting the particulate superabsorbent polymer composition to the Processing Test; and subsequent to subjecting the particulate superabsorbent polymer composition to the Processing Test the treated particulate superabsorbent polymer composition has a permeability stability index of from about 0.60 to about 0.99.

With the foregoing in mind, it is a feature and advantage of the invention to provide particulate superabsorbent polymer composition having improved permeability stability, and methods of increasing improved stability of particulate superabsorbent polymer composition. Numerous other features and advantages of the present invention will appear from the following description.

DEFINITIONS

Figure 1:
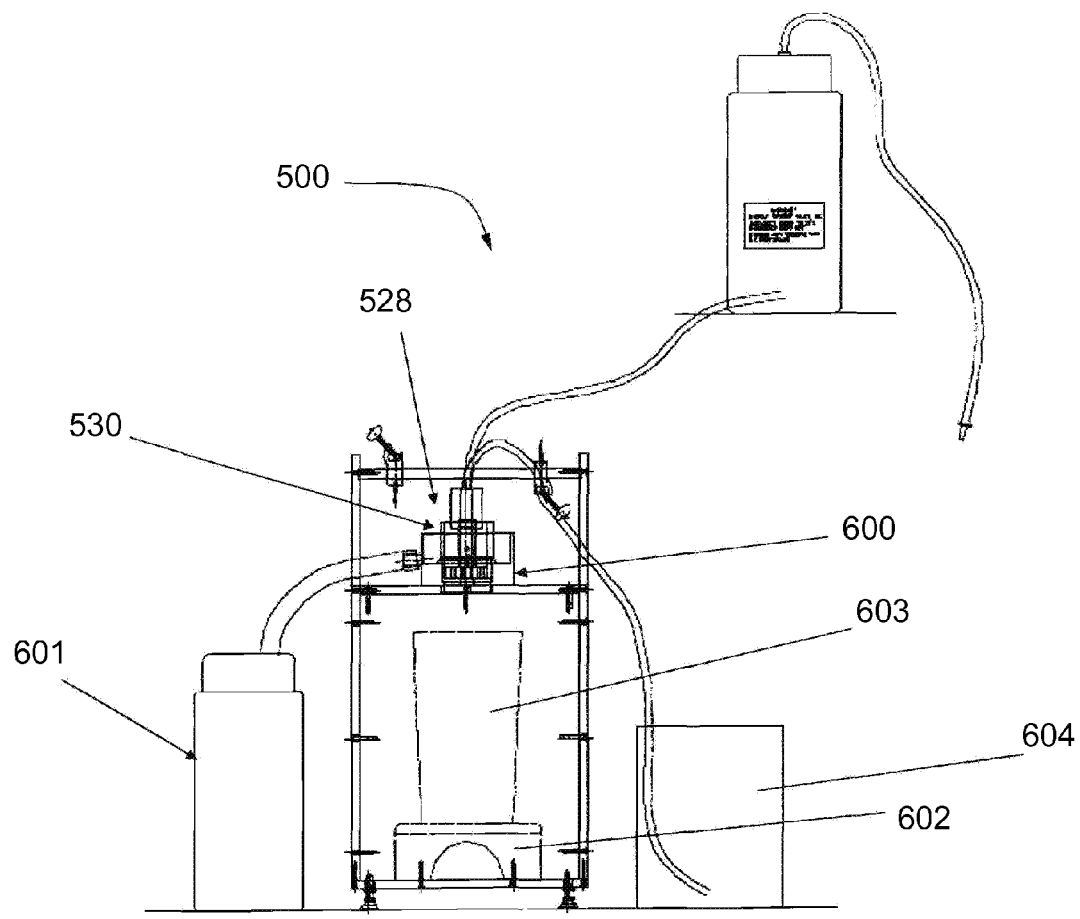
FIG. 1 is a side view of the test apparatus employed for the Free Swell Gel Bed Permeability Test.

Within the context of this specification, each term or phrase below will include the following meaning or meanings It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about," the claims include equivalents to the quantities.

The term "Centrifuge Retention Capacity (CRC)" as used herein refers to the ability of the particulate superabsorbent polymer to retain liquid therein after being saturated and subjected to centrifugation under controlled conditions and is stated as grams of liquid retained per gram weight of the sample (g/g) as measured by the Centrifuge Retention Capacity Test set forth herein.

The term "compressibility" as used herein refers to a measure of the relative volume change of the particulate superabsorbent polymer composition as a response to a pressure change as set forth in a Compressibility Test disclosed herein.

The terms "crosslinked", "crosslink", "crosslinker", or "crosslinking" as used herein refers to any means for effectively rendering normally water-soluble materials substantially water-insoluble but swellable. Such a crosslinking means can include, for example, physical entanglement, crystalline domains, covalent bonds, ionic complexes and associations, hydrophilic associations such as hydrogen bonding, hydrophobic associations, or Van der Waals forces.

The term "internal crosslinker" or "monomer crosslinker" as used herein refers to use of a crosslinker in the monomer solution to form the polymer.

The term "dry particulate superabsorbent polymer composition" as used herein generally refers to the superabsorbent polymer composition having less than about 20% moisture.

The term "gel permeability" is a property of the mass of particles as a whole and is related to particle size distribution, particle shape, and the connectedness of the open pores between the particles, shear modulus, and surface modification of the swollen gel. In practical terms, the gel permeability of the superabsorbent polymer composition is a measure of how rapidly liquid flows through the mass of swollen particles. Low gel permeability indicates that liquid cannot flow readily through the superabsorbent polymer composition, which is generally referred to as gel blocking, and that any forced flow of liquid (such as a second application of urine during use of the diaper) must take an alternate path (e.g., diaper leakage).

The terms "particle," "particulate," and the like, when used with the term "superabsorbent polymer," refer to the form of discrete units. The units can comprise flakes, fibers, agglomerates, granules, powders, spheres, pulverized materials, or the like, as well as combinations thereof. The particles can have any desired shape: for example, cubic, rod like polyhedral, spherical or semi-spherical, rounded or semi-rounded, angular, irregular, et cetera.

The terms "particulate superabsorbent polymer" and "particulate superabsorbent polymer composition" refer to the form of superabsorbent polymer and superabsorbent polymer compositions in discrete form, wherein the "particulate superabsorbent polymer" and "particulate superabsorbent polymer compositions" may have a particle size of less than 1000 μm, or from about 150 μm to about 850 μm.

The term "permeability", when used herein shall mean a measure of the effective connectedness of a porous structure, in this case, crosslinked polymers, and may be specified in terms of the void fraction, and extent of connectedness of the particulate superabsorbent polymer composition.

The term "permeability stability index" when used herein shall mean the ability of the particulate superabsorbent polymer to maintain the original permeability after being subjected to a processing test under controlled conditions. It refers to the ratio of the permeability of the processed sample to the permeability of the original sample as set forth in a Processing Test disclosed herein.

The term "polymer" includes, but is not limited to, homopolymers, copolymers, for example, block, graft, random, and alternating copolymers, terpolymers, etc., and blends and modifications thereof. Furthermore, unless otherwise specifically limited, the term "polymer" shall include all possible configurational isomers of the material. These configurations include, but are not limited to isotactic, syndiotactic, and atactic symmetries.

The term "polyolefin" as used herein generally includes, but is not limited to, materials such as polyethylene, polypropylene, polyisobutylene, polystyrene, ethylene vinyl acetate copolymer, and the like, the homopolymers, copolymers, terpolymers, etc., thereof, and blends and modifications thereof. The term "polyolefin" shall include all possible structures thereof, which include, but are not limited to, isotatic, synodiotactic, and random symmetries. Copolymers include atactic and block copolymers.

The term "superabsorbent polymer" as used herein refers to water-swellable, water-insoluble organic or inorganic materials including superabsorbent polymers and superabsorbent polymer compositions capable, under the most favorable conditions, of absorbing at least about 10 times their weight, or at least about 15 times their weight, or at least about 25 times their weight in an aqueous solution containing 0.9 weight percent sodium chloride.

The term "superabsorbent polymer composition" as used herein refers to a superabsorbent polymer comprising a surface additive in accordance with the present invention.

The term "surface crosslinking" as used herein refers to the level of functional crosslinks in the vicinity of the surface of the superabsorbent polymer particle, which is generally higher than the level of functional crosslinks in the interior of the superabsorbent polymer particle. As used herein, "surface" describes the outer-facing boundaries of the particle.

The term "thermoplastic" as used herein describes a material that softens when exposed to heat and which substantially returns to a non-softened condition when cooled to room temperature.

The term "% by weight" or "% wt" as used herein and referring to components of the dry particulate superabsorbent polymer composition, is to be interpreted as based on the weight of the dry superabsorbent polymer composition, unless otherwise specified herein.

The term "moisture content" when used herein shall mean the quantity of water contained in the particulate superabsorbent polymer composition as measured by the Moisture Content Test.

These terms may be defined with additional language in the remaining portions of the specification.

DETAILED DESCRIPTION OF THE INVENTION

While typical aspects of embodiment and/or embodiments have been set forth for the purpose of illustration, this Detailed Description and the accompanying drawings should not be deemed to be a limitation on the scope of the invention. Accordingly, various modifications, adaptations, and alternatives may occur to one skilled in the art without departing from the spirit and scope of the present invention. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

In accordance with the invention, a particulate superabsorbent polymer composition having improved stability can be achieved using the methods described herein. These particulate superabsorbent polymer compositions having improved stability have improved resistance to processing of the particulate superabsorbent polymer composition, and reduced functional loss compared to current commercially available particulate superabsorbent polymer composition.

In another embodiment, the present invention is directed to a particulate superabsorbent polymer composition having improved stability comprising a particulate superabsorbent polymer and from 0.01 wt % to about 5 wt % based on the particulate superabsorbent polymer composition weight of a neutralized aluminum salt applied to the surface of the particulate superabsorbent polymer, in the form of an aqueous neutralized aluminum salt solution having a pH value from about 5.5 to about 8; wherein the particulate superabsorbent polymer composition has a centrifuge retention capacity of from about 25 grams to about 40 grams of 0.9 weight percent sodium chloride aqueous per gram of the particulate superabsorbent polymer composition and an original Free Swell Gel Bed Permeability (FSGBP) of about $20 \times 10^{-8}$ cm$^2$ to about $200 \times 10^{-8}$ cm$^2$ prior to subjecting the treated particulate superabsorbent polymer composition to a Processing Test; and a compressibility of from about 1.30 mm$^2$/N to about 4 mm$^2$/N, and having particulate superabsorbent polymer having a particle diameter of larger than 600 μm in an amount of less than about 15 wt %, or from about 3 wt % to about 15 wt %, or from about 6 wt % to about 15 wt %, of the particulate superabsorbent polymer composition and as specified by standard sieve classification.

In addition, the present invention is directed to a particulate superabsorbent polymer composition having improved stability comprising:

a) from about 55 wt % to about 85 wt % of polymerizable unsaturated acid group containing monomers selected from acrylic acid, methacrylic acid, or 2-acrylamido-2-methylpropanesulfonic acid, or mixtures thereof;

b) from about 14 wt % to about 45 wt % of an alkali base selected from sodium hydroxide or potassium hydroxide to neutralize the polymerizable unsaturated acid group containing monomers of a) to from about 50 to about 80 mol %;

c) from about 0.001 wt % to about 5.0 wt % based on the weight of a) of an internal crosslinking agent, wherein the components a), b) and c) are polymerized into a hydrogel which is granulated into particulate superabsorbent polymer having a surface;

d) from about 0.001 wt % to about 5.0 wt % based on the particulate superabsorbent composition weight of surface crosslinking agent applied to the surface of the particulate superabsorbent polymer;

e) from 0.001 wt to about 5.0 wt % based on the particulate superabsorbent composition weight of a neutralized aluminum salt applied to the surface of the particulate superabsorbent polymer, in the form of an aqueous neutralized aluminum salt solution having a pH value from about 5.5 to about 8;

wherein the particulate superabsorbent polymer composition has a centrifuge retention capacity of from about 25 grams to about 40 grams of 0.9 weight percent sodium chloride aqueous per gram of the particulate superabsorbent polymer composition and an original Free Swell Gel Bed Permeability (FSGBP) of about $20 \times 10^{-8}$ cm$^2$ to about $200 \times 10^{-8}$ cm$^2$ prior to subjecting the treated particulate superabsorbent polymer composition to the Processing Test; and subsequent to subjecting the treated particulate superabsorbent polymer composition to the Processing Test the treated particulate superabsorbent polymer composition permeability stability index of from about 0.60 to about 0.99 and having particulate superabsorbent polymer having a particle diameter of larger than 600 μm in an amount of less than about 15 wt %, or from about 3 wt % to about 15 wt %, or from about 6 wt % to about 15 wt %, of the particulate superabsorbent polymer composition and as specified by standard sieve classification.

In another embodiment, the particulate superabsorbent polymer composition having improved stability may be prepared by a process comprising the following steps:

a) providing a particulate superabsorbent polymer;

b) preparing a neutralized aluminum salt in the form of an aqueous solution having a pH value from about 5.5 to about 8; and;

c) applying the aqueous neutralized aluminum salt solution on the surface of the particulate superabsorbent polymer; and wherein the particulate superabsorbent polymer composition has a degree of neutralization of from about 50% mol to about 80 mol %; and the particulate superabsorbent polymer composition has a Centrifuge Retention Capacity of from about 25 grams to about 40 grams of 0.9 weight percent sodium chloride aqueous per gram of the particulate superabsorbent polymer composition and a Free Swell Gel Bed Permeability (FSGBP) of about $20 \times 10^{-8}$ cm$^2$ to about $200 \times 10^{-8}$ cm$^2$ prior to subjecting the treated particulate superabsorbent polymer composition to the Processing Test; and a compressibility of from about 1.30 mm$^2$/N to about 4 mm$^2$/N wherein said particulate superabsorbent polymer composition has particles having a particle diameters of smaller than 600 µm and larger than 150 µm in an amount of not less than about 85 wt % of the particulate superabsorbent polymer composition and as specified by standard sieve classification and the particles having a weight average particle diameter (D50) specified by standard sieve classification of from 300 to 400 µm.

The present invention is also directed to a particulate superabsorbent polymer composition having improved stability comprising a particulate superabsorbent polymer and from 0.01 wt % to about 5 wt % based on the particulate superabsorbent polymer composition weight of a neutralized aluminum salt applied to the surface of the particulate superabsorbent polymer, in the form of an aqueous neutralized aluminum salt solution having a pH value from about 5.5 to about 8; wherein the particulate superabsorbent polymer composition has a centrifuge retention capacity of from about 25 grams to about 40 grams of 0.9 weight percent sodium chloride aqueous per gram of the particulate superabsorbent polymer composition and an original Free Swell Gel Bed Permeability (FSGBP) of about $20 \times 10^{-8}$ cm$^2$ to about $200 \times 10^{-8}$ cm$^2$ prior to subjecting the particulate superabsorbent polymer composition to a Processing Test; and a compressibility of from about 1.30 mm$^2$/N to about 4 mm$^2$/N and having particles having a particle diameters of larger than 600 µm in an amount of from about 6 wt % to about 15 wt % of the particulate superabsorbent polymer composition and as specified by standard sieve classification.

In addition, the present invention is directed to a particulate superabsorbent polymer composition having improved stability comprising a particulate superabsorbent polymer and from 0.01 wt % to about 5 wt % based on the particulate superabsorbent polymer composition weight of a neutralized aluminum salt applied to the surface of the particulate superabsorbent polymer, in the form of an aqueous neutralized aluminum salt solution having a pH value from about 5.5 to about 8; wherein said particulate superabsorbent polymer composition has particles having a particle diameters of smaller than 600 µm and larger than 150 µm in an amount of not less than about 85 wt % of the particulate superabsorbent polymer composition and as specified by standard sieve classification and the particles having a weight average particle diameter (D50) specified by standard sieve classification of from 300 to 400 µm.

A suitable superabsorbent polymer may be selected from synthetic, natural, biodegradable, and modified natural polymers. The term crosslinked used in reference to the superabsorbent polymer refers to any means for effectively rendering normally water-soluble materials substantially water-insoluble but swellable. Such a crosslinking means can include for example, physical entanglement, crystalline domains, covalent bonds, ionic complexes and associations, hydrophilic associations such as hydrogen bonding, hydrophobic associations or Van der Waals forces. Superabsorbent polymers include internal crosslinking and may further include surface crosslinking.

A superabsorbent polymer as set forth in embodiments of the present invention can be obtained by the initial polymerization of from about 55% to about 99.9 wt % of the superabsorbent polymer of polymerizable unsaturated acid group containing monomer. A suitable monomer includes any of those containing carboxyl groups, such as acrylic acid or methacrylic acid; or 2-acrylamido-2-methylpropanesulfonic acid, or mixtures thereof. It is desirable for at least about 50 wt %, and more desirable for at least about 75 wt % of the acid groups to be carboxyl groups.

The process to make a superabsorbent polymer as set forth in embodiments of the present invention may be obtained by the initial polymerization of from about 55% to about 99.9 wt % of the superabsorbent polymer of polymerizable unsaturated acid group containing monomer. A suitable polymerizable monomer includes any of those containing carboxyl groups, such as acrylic acid, methacrylic acid, or 2-acrylamido-2-methylpropanesulfonic acid, or mixtures thereof. It is desirable for at least about 50% by weight, and more desirable for at least about 75 wt % of the acid groups to be carboxyl groups.

The acid groups are neutralized with an alkali base to the extent of at least about 25 mol %, or from about 50 mol % to about 80 mol %, that is, the acid groups are desirably present as sodium, potassium, or ammonium salts. The amount of alkali base may be from about 14 wt % to about 45 wt % of the particulate superabsorbent polymer composition. The alkali base may include sodium hydroxide or potassium hydroxide. In some aspects, it is desirable to utilize polymers obtained by polymerization of acrylic acid or methacrylic acid, the carboxyl groups of which are neutralized in the presence of internal cross linking agents. It is noted that the neutralization may be achieved by either adding the alkali base to the monomer solution or adding the monomer such as acrylic acid to the alkali base.

In some aspects, the second suitable monomer that can be copolymerized with the ethylenically unsaturated monomer may include, but is not limited to acrylamide, methacrylamide, hydroxyethyl acrylate, dimethylaminoalkyl (meth)-acrylate, ethoxylated (meth)-acrylates, dimethylaminopropylacrylamide, or acrylamidopropyltrimethylammonium chloride. Such monomer may be present in a range of from 0 wt % to about 40 wt % of the copolymerized monomer.

In the case when the monomer is acrylic acid, the partially neutralized, acrylate salt is turned into the polymer in the particulate water absorbing agent following polymerization, the converted value based on acrylic acid may be determined through converting the partially neutralized polyacrylate salt is assumed to be entirely the equimolar unneutralized polyacrylic acid.

The superabsorbent polymer of the invention also includes from about 0.001 wt % to about 5 wt % by weight or from about 0.2 wt % to about 3 wt % based on the total amount of the polymerizable unsaturated acid group containing monomer of at least one internal cross linking agent. The internal crosslinking agent generally has at least two ethylenically unsaturated double bonds or one ethylenically unsaturated double bond and one functional group which is reactive towards acid groups of the polymerizable unsaturated acid group containing monomers or several functional groups which are reactive towards acid groups can be used as the internal crosslinking component and which is present during the polymerization of the polymerizable unsaturated acid group containing monomers.

Examples of internal crosslinking agents used in superabsorbent polymers include aliphatic unsaturated amides, such as methylenebisacryl- or -methacrylamide or ethylenebisacrylamide, and furthermore aliphatic esters of polyols or alkoxylated polyols with ethylenically unsaturated acids, such as di(meth)acrylates or tri(meth)acrylates of butanediol or ethylene glycol, polyglycols or trimethylolpropane, di- and triacrylate esters of trimethylolpropane which is preferably oxyalkylated, preferably ethoxylated, with 1 to 30 mol of alkylene oxide, acrylate and methacrylate esters of glycerol and pentaerythritol and of glycerol and pentaerythritol oxyethylated with preferably 1 to 30 mol of ethylene oxide and furthermore allyl compounds, such as allyl (meth)acrylate, alkoxylated allyl (meth)acrylate reacted with preferably 1 to 30 mol of ethylene oxide, triallyl cyanurate, triallyl isocyanurate, maleic acid diallyl ester, poly-allyl esters, vinyl trimethoxysilane, vinyl triethoxysilane, polysiloxane comprising at least two vinyl groups, tetraallyloxyethane, tetraallyloxyethane, triallylamine, tetraallylethylenediamine, diols, polyols, hydroxy allyl or acrylate compounds and allyl esters of phosphoric acid or phosphorous acid, and furthermore monomers which are capable of crosslinking, such as N-methylol compounds of unsaturated amides, such as of methacrylamide or acrylamide, and the ethers derived there from. Ionic crosslinkers such as aluminum metal salts may also be employed. Mixtures of the crosslinking agents mentioned can also be employed.

In another embodiment, the superabsorbent polymer may include from about 0.001 wt % to about 0.1 wt % based on the total amount of the polymerizable unsaturated acid group containing monomer of a second internal crosslinker which may comprise compositions comprising at least two ethylenically unsaturated double-bonds, for example, methylenebisacrylamide or -methacrylamide or ethylenebisacrylamide; additionally, esters of unsaturated mono- or polycarboxylic acids of polyols, such as, diacrylates or triacrylates, e.g., butanediol- or ethylene glycol diacrylate or -methacrylate; trimethylolpropane triacrylate, as well as their alkoxylated derivatives; additionally, allyl compounds, such as allyl (meth)acrylate, triallyl cyanurate, maleic acid diallyl ester, polyallyl ester, tetraallyloxyethane, di- and triallylamine, tetrallylethylenediamine, allyl esters of phosphoric acid or phosphorous acid. Moreover, compounds having at least one functional group reactive towards acid groups may also be used. Examples thereof include N-methylol compounds of amides, such as methacrylamide or acrylamide, and the ethers derived there from, as well as di- and polyglycidyl compounds.

The usual initiators, such as e.g. azo or peroxo compounds, redox systems or UV initiators, (sensitizers), and/or radiation are used for initiation of the free-radical polymerization. In some aspects, initiators can be used for initiation of the free-radical polymerization. Suitable initiators include, but are not limited to, azo or peroxo compounds, redox systems or ultraviolet initiators, sensitizers, and/or radiation.

The polymerization forms a superabsorbent polymer gel, which is granulated into superabsorbent polymer particles, or particulate superabsorbent polymer. The superabsorbent polymer gel generally has moisture content of from about 40 to 80 wt % of the superabsorbent polymer gel. The particulate superabsorbent polymer generally includes particle sizes ranging from about 50 µm to about 1000 µm, or from about 150 µm to about 850 µm. The present invention may include at least about 40 wt % of the particles having a particle size from about 300 µm to about 600 µm, at least about 50 wt % of the particles having a particle size from about 300 µm to about 600 µm, or at least about 60 wt % of the particles having a particle size from about 300 µm to about 600 µm as measured by screening through a U.S. standard 30 mesh screen and retained on a U.S. standard 50 mesh screen. In addition, the size distribution of the superabsorbent polymer particles of the present invention may include less than about 30% by weight of particles having a size greater than about 600 µm, and less than about 30% by weight of particles having a size of less than about 300 µm, and from 0 to 5 weight % of the particles less than 150 µm, as measured using for example a RO-TAP® Mechanical Sieve Shaker Model B available from W. S. Tyler, Inc., Mentor Ohio.

In another embodiment of the particulate superabsorbent polymer of the present invention, the diameter of the resin particle is set as follows. The mass average particle diameter is generally from about 200 to about 450 µm, or from about 300 to about 430 µm, or from about 300 to about 400 µm, or from about 350 to about 400 µm, or from about 360 to about 400 µm, or from about 370 to about 400 µm. Further, the percentage of particles less than 150 µm is generally from 0 to about 8% by weight, or from 0 to about 5% by weight, or from 0 to about 3% by weight, or from 0 to about 1% by weight. Further, the percentage of particles more than 600 µm is generally from 0 to about 25% by weight, or from 3 to about 15% by weight, or from 5 to about 12% by weight, or from 5 to about 8% by weight.

The particle size may be adjusted by subjecting the particles to dispersion polymerization and dispersion drying. However, in general, when carrying out aqueous polymerization in particular, the particles are pulverized and classified after drying, and then mass average diameter of D50, and the amount of particles smaller than 150 µm and larger than 600 µm, is adjusted so as to obtain a specific particle size distribution. For example, if the specific particle size distribution is achieved by decreasing the diameter of the particles having mass average diameter of D50 to 400 µm or smaller and also reducing the amount of the fine particles having diameter less than 150 µm and larger than 600 µm, the particles may be first classified into coarse particles and fine particles after drying by using a general classifying equipment such as a sieve. This process preferably removes coarse particles with a diameter of 5000 µm to 600 µm, or of 2000 µm to 600 µm, or of 1000 µm to 600 µm. Then, in the main adjustment process, the fine particles with a diameter less than 150 µm are removed. The removed coarse particles may be discarded, but they are more likely to be pulverized again through the foregoing pulverizing process. The resulting particulate superabsorbent polymer thus produced with a specific particle size distribution through the pulverizing process is therefore constituted of irregularly-pulverized particles.

The particulate superabsorbent polymers are surface treated with additional chemicals and treatments as set forth herein. In particular, the surface of the particulate superabsorbent polymer is crosslinked, generally referred to as surface crosslinking, by the addition of a surface crosslinking agent and heat-treatment. In general, surface crosslinking is a process to increase the crosslink density of the polymer matrix in the vicinity of the particulate superabsorbent polymer surface with respect to the crosslinking density of the particle interior. The amount of the surface crosslinking agent may be present in an amount of from about 0.01 wt % to about 5 wt % of the dry particulate superabsorbent polymer composition, and such as from about 0.1 wt % to about 3 wt %, and such as from about 0.1 wt % to about 1 wt % by weight, based on the weight of the dry particulate superabsorbent polymer composition.

Desirable surface crosslinking agents include chemicals with one or more functional groups that are reactive toward pendant groups of the polymer chains, typically the acid groups. Surface crosslinker agents comprise functional groups which react with functional groups of a polymer structure in a condensation reaction (condensation crosslinker), in an addition reaction or in a ring opening reaction. These compounds may include, for example, diethylene glycol, triethylene glycol, polyethylene glycol, glycerine, polyglycerine, propylene glycol, diethanolamine, triethanolamine, polyoxypropylene, oxyethylene-oxypropylene block copolymers, sorbitan fatty acid esters, polyoxyethylene sorbitan fatty acid esters, trimethylolpropane, pentaerythritol, polyvinyl alcohol, sorbitol, 1,3-dioxolan-2-one (ethylene carbonate), 4-methyl-1,3-dioxolan-2-one (propylene carbonate), or 4,5-dimethyl-1,3-dioxolan-2-one.

After the particulate superabsorbent polymer has been brought into contact with the surface crosslinker agent, or with the fluid comprising the surface crosslinker agent, the treated particulate superabsorbent polymer is heat treated to a temperature of from about 50 to about 300° C., or from about 75 to about 275° C., or from about 150 to about 250° C., and for a time of from about 5 to about 90 minutes dependent on the temperature, so that the outer region of the polymer structures is more strongly crosslinked compared to the inner region (i.e., surface crosslinking). The duration of the heat treatment is limited by the risk that the desired property profile of the polymer structures will be destroyed as a result of the effect of heat.

In one particular aspect of surface crosslinking, the particulate superabsorbent polymer is surface-treated with ethylene carbonate followed by heating to affect surface crosslinking of the superabsorbent polymer particle, which improves the surface crosslinking density and the gel strength characteristics of the particulate superabsorbent polymer. More specifically, the surface crosslinking agent is coated onto the particulate superabsorbent polymer by mixing the particulate superabsorbent polymer with an aqueous alcoholic solution of the ethylene carbonate surface crosslinking agent. The amount of alcohol in the aqueous alcoholic solution may be determined by the solubility of the alkylene carbonate and is kept as low as possible for various reasons, for instance, for protection against explosions. Suitable alcohols are methanol, isopropanol, ethanol, butanol, or butyl glycol, as well as mixtures of these alcohols. In some aspects, the solvent desirably is water, which typically is used in an amount of about 0.3% by weight to about 5.0 wt %, based on the weight of the dry particulate superabsorbent polymer composition. In still other aspects, the ethylene carbonate surface crosslinking agent may be applied from a powder mixture, for example, with an inorganic carrier material, such as silicone dioxide ($SiO_2$), or in a vapor state by sublimation of the ethylene carbonate.

To achieve the desired surface crosslinking properties, the surface crosslinking agents such as ethylene carbonate should be distributed evenly on the particulate superabsorbent polymer. For this purpose, mixing is effected in suitable mixers known in the art, such as fluidized bed mixers, paddle mixers, rotary drum mixers, or twin-worm mixers. It is also possible to carry out the coating of the particulate superabsorbent polymer during one of the process steps in the production of the particulate superabsorbent polymer. In one particular aspect, a suitable process for this purpose is the inverse suspension polymerization process.

The solution of the surface crosslinking agent may also include a from 0 wt % to about 1 wt %, or from about 0.01 wt % to about 0.5 wt % based on the dry particulate superabsorbent polymer composition of a thermoplastic polymer. Examples of thermoplastic polymers include polyolefin, polyethylene, polyester, linear low density polyethylene (LLDPE), ethylene acrylic acid copolymer (EAA), ethylene alkyl methacrylate copolymer (EMA), polypropylene (PP), maleated polypropylene, ethylene vinyl acetate copolymer (EVA), polyester, and blends of all families of polyolefins, such as blends of PP, EVA, EMA, EEA, EBA, HDPE, MDPE, LDPE, LLDPE, and/or VLDPE, may also be advantageously employed. The term polyolefin as used herein is defined above. In particular aspects, maleated polypropylene is a preferred thermoplastic polymer for use in the present invention. A thermoplastic polymer may be functionalized to have additional benefits such as water solubility or dispersability.

The heat treatment, which follows the coating treatment of the particulate superabsorbent polymer, may be carried out as follows. In general, the heat treatment is at a temperature of from about 100° C. to about 300° C. Lower temperatures are possible if highly reactive epoxide crosslinking agents are used. However, if an ethylene carbonate is used, then the thermal treatment is suitably at a temperature of from about 150° C. to about 250° C. In this particular aspect, the treatment temperature depends on the dwell time and the kind of ethylene carbonate. For example, at a temperature of about 150° C., the thermal treatment is carried out for one hour or longer. In contrast, at a temperature of about 250° C., a few minutes (e.g., from about 0.5 minutes to about 5 minutes) are sufficient to achieve the desired surface crosslinking properties. The thermal treatment may be carried out in conventional dryers or ovens known in the art.

In addition to surface crosslinking, the particulate superabsorbent polymer compositions may be further surface treated with other chemical compositions. The particulate superabsorbent polymer composition according to the invention comprises from about 0.01 wt % to about 5 wt % based on the particulate superabsorbent composition weight of a aluminum salt applied to the surface of the particulate superabsorbent polymer, in the form of an aqueous solution having a pH value from about 5.5 to about 8, or from about 6 to about 7. Or, the particulate superabsorbent polymer composition comprises from about 6 wt % to about 15 wt % based on the particulate superabsorbent composition weight of an aqueous aluminum salt solution applied to the surface of the surface crosslinked particulate superabsorbent polymer, wherein the aqueous aluminum salt solution has a pH value from about 5.5 to about 8, or from about 6 to about 7. The aqueous solution of the aluminum salt may comprise an aluminum cation and a hydroxyl ion or an anion of a deprotonated hydroxyl organic acid. Examples of preferred organic acids are hydroxyl monocarboxylic acids such as lactic acid, glycolic acid, gluconic acid, or 3-hydroxypropionic acid.

In addition, a superabsorbent polymer composition with significantly improved stability including resistance to damage control is unexpectedly obtained by coating the superabsorbent polymer with the aluminum salt solution having adjusted pH of about 5.5 to about 8, or from about 6 to about 7, and appropriate concentration and amount. The aqueous aluminum salt solution includes the reaction product of alkali hydroxide and aluminum sulfate or aluminum sulfate hydrate. In another embodiment, the aqueous aluminum salt solution includes the reaction product of sodium hydroxide and aluminum sulfate or aluminum sulfate hydrate. In yet another embodiment, the aqueous aluminum salt solution comprises an aluminum compound and an organic acid. The mixture of the aluminum compound with the organic acid (salt) can be acidic or basic. And the pH can be adjusted to the desired range with a basic or acidic material. Examples of the basic materials for pH adjustment include but not limited to sodium hydroxide, potassium hydroxide, ammonium hydroxide, sodium carbonate or sodium bicarbonate. Examples of the acidic materials for pH adjustment include but are not limited to hydrochloric acid, sulfuric acid, methylsulfonic acid, or carbon dioxide in water. The acidic aluminum salts, such as aluminum chloride, aluminum sulfate, aluminum nitrate and polyaluminum chloride, or the basic aluminum salts, such as sodium aluminate, potassium aluminate and ammonium aluminate, may be used for pH adjustment as well.

The aqueous aluminum salt solution may be added at various stages of surface treatment of the particulate superabsorbent polymer. In one embodiment, the aqueous aluminum salt solution may be applied to the particulate superabsorbent polymer along with the surface crosslinking solution.

The aqueous aluminum salt solution may be added after the surface crosslinking step, which may be called a post treatment. In one embodiment, the surface crosslinked particulate superabsorbent polymer and the aluminum salt are mixed using means well known to those skilled in the art. In particular, from about 6 wt % to about 15 wt % of an aqueous aluminum salt solution is applied to a surface crosslinked particulate superabsorbent polymer composition.

The particulate superabsorbent polymer composition having improved stability may include from about 0 wt % to about 5 wt %, or from about 0.001 wt % to about 3 wt %, or from about 0.01 wt % to about 2 wt % based on the weight of the dry particulate superabsorbent polymer composition of a cationic polymer. A cationic polymer as used herein refers to a polymer or mixture of polymers comprising a functional group or groups having a potential of becoming positively charged ions upon ionization in an aqueous solution. Suitable functional groups for a cationic polymer include, but are not limited to, primary, secondary, or tertiary amino groups, imino groups, imido groups, amido groups, and quaternary ammonium groups. Examples of synthetic cationic polymers include the salts or partial salts of poly(vinyl amines), poly(allylamines), or poly(ethylene imine). Examples of natural-based cationic polymers include partially deacetylated chitin, chitosan, and chitosan salts.

The particulate superabsorbent polymer composition having improved stability may include from about 0 wt % to about 5 wt %, or from about 0.001 wt % to about 3 wt %, or from about 0.01 wt % to about 2 wt % based on the weight of the dry particulate superabsorbent polymer composition of water-insoluble, inorganic powder. Examples of insoluble, inorganic powders include silicon dioxide, silica, titanium dioxide, aluminum oxide, magnesium oxide, zinc oxide, talc, calcium phosphate, clays, diatomaceous earth, zeolites, bentonite, kaolin, hydrotalcite, activated clays, etc. The insoluble inorganic powder additive may be a single compound or a mixture of compounds selected from the above list. Examples of silica include fumed silica, precipitated silica, silicon dioxide, silicic acid, and silicates. In some particular aspects, microscopic noncrystalline silicon dioxide is desirable. Products include SIPERNAT® 22S and AEROSIL® 200 available from Evonik Corporation, Parsippany, N.J. In some aspects, the particle diameter of the inorganic powder can be 1,000 μm or smaller, such as 100 μm or smaller.

The particulate superabsorbent polymer composition having improved stability may also include from 0 wt % to about 30 wt %, or from about 0.001 wt % to about 25 wt %, or from about 0.01 wt % to about 20 wt % based on the weight of the dry particulate superabsorbent polymer composition, of water-soluble polymers, such as partly or completely hydrolyzed polyvinyl acetate, polyvinylpyrrolidone, starch or starch derivatives, polyglycols or polyacrylic acids, preferably in polymerized-in form. The molecular weight of these polymers is not critical as long as they are water-soluble. Preferred water-soluble polymers are starch and polyvinyl alcohol. The preferred content of such water-soluble polymers in the absorbent polymer according to the invention is 0-30 wt %, or 0-5 wt %, based on the total amount of the dry particulate superabsorbent polymer composition. The water-soluble polymers, preferably synthetic polymers, such as polyvinyl alcohol, can also serve as a graft base for the monomers to be polymerized.

The particulate superabsorbent polymer composition having improved stability may also include from 0 wt % to about 5 wt %, or from about 0.001 wt % to about 3 wt %, or from about 0.01 wt % to about 2 wt % based on the weight of the dry particulate superabsorbent polymer composition, of dedusting agents, such as hydrophilic and hydrophobic dedusting agents such as those described in U.S. Pat. Nos. 6,090,875 and 5,994,440.

In some aspects, additional surface additives may optionally be employed with the particulate superabsorbent polymer composition having improved permeability stability, such as odor-binding substances, such as cyclodextrins, zeolites, inorganic or organic salts, and similar materials; anti-caking additives, flow modification agents, surfactants, viscosity modifiers, and the like.

The particulate superabsorbent polymer composition having improved stability of the present invention may be, after the heat treatment step, treated with an aqueous solution, such as the aqueous solution of deprotonated organic acid salt, aluminum salt, or water soluble polymer such as polyethylene glycol. The treated particulate superabsorbent polymer composition has moisture content of from about 3 wt % to about 15 wt %, or from about 4 wt % to about 12 wt %, or from 5 wt % to about 11 wt % based on the particulate superabsorbent polymer composition.

The particulate superabsorbent polymer composition having improved stability according to the invention may be desirably prepared by various methods disclosed in the art including the following methods and exemplified in the Examples. The particulate superabsorbent polymer composition may be prepared continuously or discontinuously in a large-scale industrial manner, the post treatment being carried out according to the invention.

According to one method, the monomer is partially neutralized by either adding an alkali base such as sodium hydroxide to the monomer or by adding the monomer to an alkali base solution. Then the partially neutralized monomer, such as acrylic acid, is converted into a gel by free-radical polymerization in aqueous solution in the presence of crosslinking agents and any further components, and the gel is comminuted, dried, ground, and sieved off to the desired particle size, thereby forming a particulate superabsorbent polymer. This polymerization can be carried out continuously or discontinuously.

For the present invention, the size of the high-capacity superabsorbent polymer composition particles is dependent on manufacturing processes including milling and sieving. It is well known to those skilled in the art that particle size distribution of the particulate superabsorbent polymer resembles a normal distribution or a bell shaped curve. It is also known that for various reasons, the normal distribution of the particle size distribution may be skewed in either direction.

According to another method to make particulate superabsorbent polymer, inverse suspension and emulsion polymerization can also be used for preparation of the products according to the invention. According to these processes, an aqueous, partly neutralized solution of monomer, such as acrylic acid, is dispersed in a hydrophobic, organic solvent with the aid of protective colloids and/or emulsifiers, and the polymerization is started by free radical initiators. The internal crosslinking agents may be either dissolved in the monomer solution and are metered in together with this, or are added separately and optionally during the polymerization.

The addition of a water-soluble polymer as the graft base optionally takes place via the monomer solution or by direct introduction into the oily phase. The water is then removed azeotropically from the mixture, and the polymer is filtered off and optionally dried. Internal crosslinking can be carried out by polymerizing-in a polyfunctional crosslinking agent dissolved in the monomer solution and/or by reaction of suitable crosslinking agents with functional groups of the polymer during the polymerization steps.

The particulate superabsorbent polymer composition having improved stability of the present invention exhibits certain characteristics, or properties, as measured by Free Swell Gel Bed Permeability (FSGBP), Centrifuge Retention Capacity (CRC), absorbency under load at about 0.9 psi (0.9 psi AUL) and Compressibility. The FSGBP Test is a measurement of the permeability of a swollen bed of particulate superabsorbent polymer composition in terms of $10^{-8}$ cm$^2$ (e.g., separate from the absorbent structure) under a confining pressure after what is commonly referred to as "free swell" conditions. In this context, the term "free swell" means that the particulate superabsorbent polymer composition is allowed to swell without a swell restraining load upon absorbing test solution as will be described.

Permeability is a measure of the effective connectedness of a porous structure, be it a mat of fiber or a slab of foam or, in the case of this application, particulate superabsorbent polymer and particulate superabsorbent polymer composition, generally referred to as particulate superabsorbent polymer compositions herein, or SAP, and may be specified in terms of the void fraction and extent of connectedness of the particulate superabsorbent polymer compositions. Gel permeability is a property of the mass of particulate superabsorbent polymer compositions as a whole and is related to particle size distribution, particle shape, the connectedness of the open pores, shear modulus and surface modification of the swollen gel. In practical terms, the permeability of the particulate superabsorbent polymer composition is a measure of how rapidly liquid flows through the mass of swollen particles. Low permeability indicates that liquid cannot flow readily through the particulate superabsorbent polymer compositions, which is generally referred to as gel blocking, and that any forced flow of liquid (such as a second application of urine during use of the diaper) must take an alternate path (e.g., diaper leakage).

The Centrifuge Retention Capacity (CRC) Test measures the ability of the particulate superabsorbent polymer composition to retain liquid therein after being saturated and subjected to centrifugation under controlled conditions. The resultant retention capacity is stated as grams of liquid retained per gram weight of the sample (g/g).

The Absorbency Under Load (AUL) Test measures the ability of the particulate superabsorbent polymer composition particles to absorb a 0.9 weight percent solution of sodium chloride in distilled water at room temperature (test solution) while the material is under a load of 0.9 psi.

The Compressibility Test measures the relative volume change of the particulate superabsorbent polymer composition as a response to a pressure change and is performed on original particulate superabsorbent polymer composition, or shortly after the particulate superabsorbent polymer composition is manufactured.

All values of Centrifuge Retention Capacity, Absorbency Under Load and Gel Bed Permeability set forth herein are to be understood as being determined by the Centrifuge Retention Capacity Test, Absorbency Under Load Test, Free Swell Gel Bed Permeability Test and Compressibility Test as provided herein.

The particulate superabsorbent polymer composition having improved stability made by a process of the present invention may have a centrifuge retention capacity of from about 25 g/g to about 40 g/g, or from about 27 to about 35 g/g; and an absorbency under load at 0.9 psi of from about 15 g/g to about 24 g/g, or from about 16 g/g to about 22 g/g, a compressibility of from about 1.30 mm$^2$/N to about 4 mm$^2$/N, or from about 1.30 mm$^2$/N to about 3.5 mm$^2$/N, a permeability stability index of from about 0.60 to about 0.99, or from about 0.70 to about 0.97, and an original Free Swell Gel Bed Permeability (FSGBP) of about $20 \times 10^{-8}$ cm$^2$ to about $200 \times 10^{-8}$ cm$^2$ prior to subjecting the treated particulate superabsorbent polymer composition to a Processing Test and subsequent to subjecting the particulate superabsorbent polymer composition to the Processing Test the particulate superabsorbent polymer composition has a permeability stability index of from about 0.60 to about 0.99, or from about 0.70 to about 0.97. In addition, the particulate superabsorbent polymer composition has an absorbency against pressure (AAP) of 4.8 kPa for the physiological saline solution being not more than 20 g/g, or from 15 g/g to 20 g/g.

The particulate superabsorbent polymer composition according to the present invention generally has a particle size of from about 150 μm to about 850 μm and comprises from about 1 to about 40 wt % of the particulate superabsorbent polymer composition having a particle size of more than 600 μm or from about 1 to about 35 wt % of the particulate superabsorbent polymer composition having a particle size of more than 600 μm, or from about 12 wt % to about 25 wt % of the particulate superabsorbent polymer composition having a particle size of more than 600 μm, or less than about 15 wt % of the particulate superabsorbent polymer composition having a particle size of more than 600 μm and as specified by the standard sieve classification. In addition, the particulate superabsorbent polymer composition according to the present invention may have a weight average particle diameter (D50) as specified by standard sieve classification of from about 300 to about 400 μm, or from about 350 to about 400 μm, or from about 360 to about 400 μm, or from about 370 to about 400 μm.

The particulate superabsorbent polymer compositions according to the present invention can be employed in many absorbent articles including sanitary towels, diapers, or wound coverings, and they have the property that they rapidly absorb large amounts of menstrual blood, urine, or other body fluids. Since the agents according to the invention retain the absorbed liquids even under pressure and are also capable of distributing further liquid within the construction in the swollen state, they are more desirably employed in higher concentrations, with respect to the hydrophilic fiber material, such as fluff, when compared to conventional current superabsorbent compositions. They are also suitable for use as a homogeneous superabsorber layer without fluff content within the diaper construction, as a result of which particularly thin articles are possible. The polymers are furthermore suitable for use in hygiene articles (e.g., incontinence products) for adults.

The polymers according to the invention are also employed in absorbent articles that are suitable for further uses. In particular, the polymers of this invention can be used in absorbent compositions for absorbents for water or aqueous liquids, preferably in constructions for absorption of body fluids, in foamed and non-foamed sheet-like structures, in packaging materials, in constructions for plant growing, as soil improvement agents or as active compound carriers. For this, they are processed to a web by mixing with paper or fluff or synthetic fibers or by distributing the superabsorbent polymers between substrates of paper, fluff or non-woven textiles or by processing into carrier materials.

Test Procedures

Centrifuge Retention Capacity Test (CRC)

The CRC Test measures the ability of the particulate superabsorbent polymer composition to retain liquid therein after being saturated and subjected to centrifugation under controlled conditions. The resultant retention capacity is stated as grams of liquid retained per gram weight of the sample, (g/g). The CRC Test can be performed either before or after subjecting the particulate superabsorbent polymer composition to a Processing Test, as set forth herein. The sample to be tested is prepared from particles that are pre-screened through a U.S. standard 30-mesh screen and retained on a U.S. standard 50-mesh screen. As a result, the particulate superabsorbent polymer composition sample comprises particles sized in the range of about 300 to about 600 microns. The particles can be pre-screened by hand or automatically.

The retention capacity is measured by placing about 0.20 grams of the pre-screened particulate superabsorbent polymer composition sample into a water-permeable bag that will contain the sample while allowing a test solution (0.9 weight percent sodium chloride in distilled water) to be freely absorbed by the sample. A heat-sealable tea bag material, such as that available from Dexter Corporation (having a place of business in Windsor Locks, Conn., U.S.A.) as model designation 1234T heat sealable filter paper works well for most applications. The bag is formed by folding a 5-inch by 3-inch sample of the bag material in half and heat-sealing two of the open edges to form a 2.5-inch by 3-inch rectangular pouch. The heat seals are about 0.25 inches inside the edge of the material. After the sample is placed in the pouch, the remaining open edge of the pouch is also heat-sealed. Empty bags are also made to serve as controls. Three samples are prepared for each particulate superabsorbent polymer composition to be tested.

The sealed bags are submerged in a pan containing the test solution at about 23° C., making sure that the bags are held down until they are completely wetted. After wetting, the particulate superabsorbent polymer composition samples remain in the solution for about 30 minutes, at which time they are removed from the solution and temporarily laid on a non-absorbent flat surface.

The wet bags are then placed into the basket wherein the wet bags are separated from each other and are placed at the outer circumferential edge of the basket, wherein the basket is of a suitable centrifuge capable of subjecting the samples to a g-force of about 350. One suitable centrifuge is a CLAY ADAMS DYNAC II, model #0103, having a water collection basket, a digital rpm gauge, and a machined drainage basket adapted to hold and drain the flat bag samples. Where multiple samples are centrifuged, the samples are placed in opposing positions within the centrifuge to balance the basket when spinning. The bags (including the wet, empty bags) are centrifuged at about 1,600 rpm (e.g., to achieve a target g-force of about 350 g force with a variance from about 240 to about 360 g force), for 3 minutes. G force is defined as an unit of inertial force on a body that is subjected to rapid acceleration or gravity, equal to 32 ft/sec² at sea level. The bags are removed and weighed, with the empty bags (controls) being weighed first, followed by the bags containing the particulate superabsorbent polymer composition samples. The amount of solution retained by the particulate superabsorbent polymer composition sample, taking into account the solution retained by the bag itself, is the centrifuge retention capacity (CRC) of the superabsorbent polymer, expressed as grams of fluid per gram of superabsorbent polymer. More particularly, the retention capacity is determined by the following equation:

$$CRC = [\text{sample bag after centrifuge} - \text{empty bag after centrifuge} - \text{dry sample weight}]/\text{dry sample weight}$$

The three samples are tested, and the results are averaged to determine the CRC of the particulate superabsorbent polymer composition.

Free-Swell Gel Bed Permeability Test (FSGBP)

Figure 2:
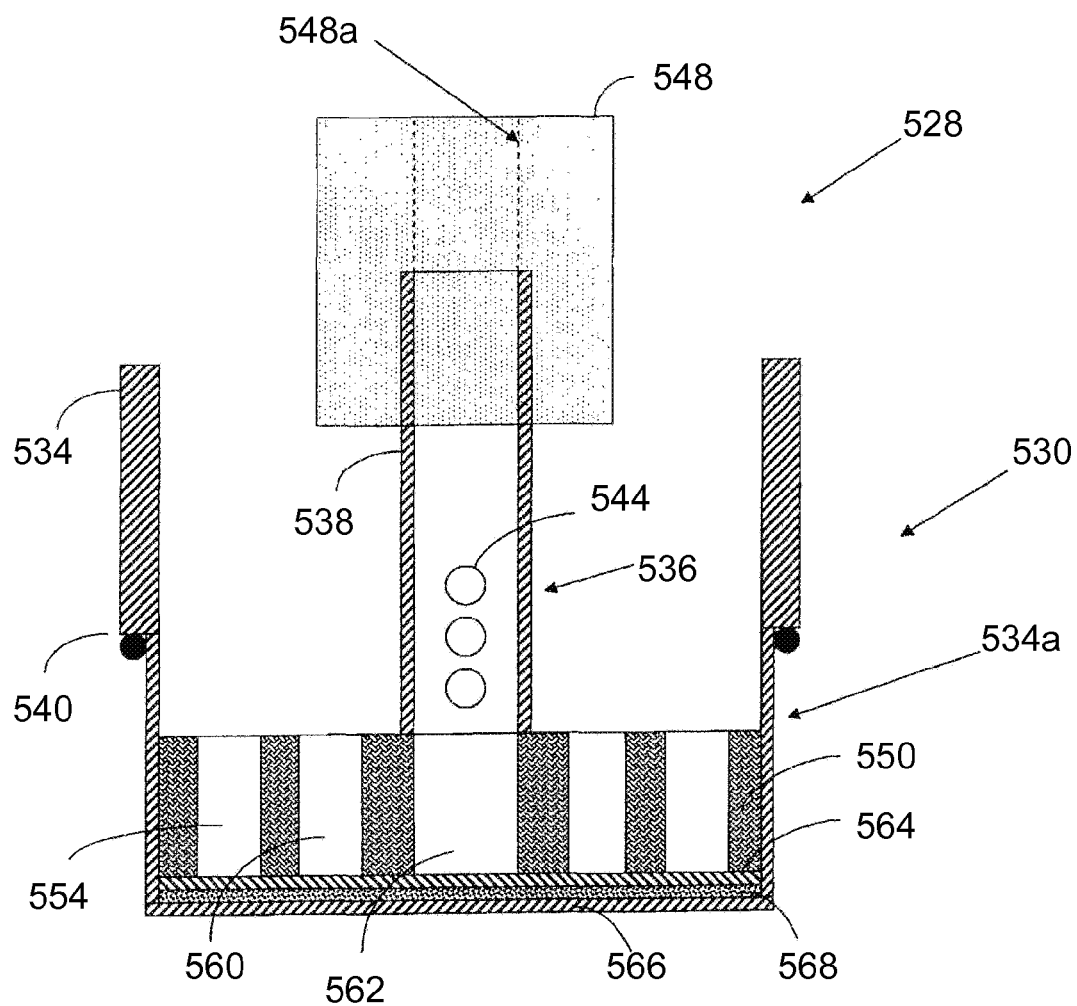
FIG. 2 is a cross-sectional side view of a cylinder/cup assembly employed in the Free Swell Gel Bed Permeability Test apparatus shown in FIG. 1.
Figure 3:
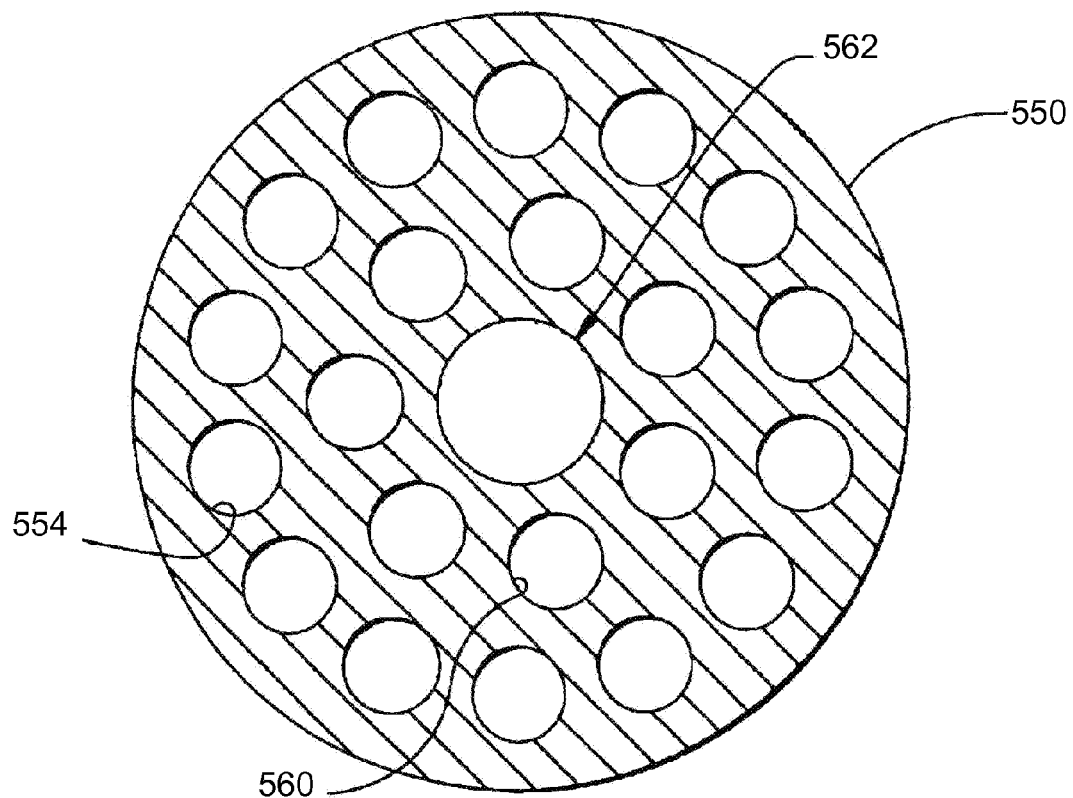
FIG. 3 is a top view of a plunger employed in the Free Swell Gel Bed Permeability Test apparatus shown in FIG. 1.

As used herein, the Free-Swell Gel Bed Permeability Test, also referred to as the Gel Bed Permeability Under 0 psi Swell Pressure Test (FSGBP), determines the permeability of a swollen bed of gel particles (e.g., such as the particulate superabsorbent polymer composition, or the particulate superabsorbent polymer prior to being surface treated), under what is commonly referred to as "free swell" conditions. The term "free swell" means that the gel particles are allowed to swell without a restraining load upon absorbing test solution as will be described. A suitable apparatus for conducting the Gel Bed Permeability Test is shown in FIGS. 1, 2, and 3 and indicated generally as 500. The test apparatus assembly 528 comprises a sample container, generally indicated at 530, and a plunger, generally indicated at 536. The plunger comprises a shaft 538 having a cylinder hole bored down the longitudinal axis and a head 550 positioned at the bottom of the shaft. The shaft hole 562 has a diameter of about 16 mm. The plunger head is attached to the shaft, such as by adhesion. Twelve holes 544 are bored into the radial axis of the shaft, three positioned at every 90 degrees having diameters of about 6.4 mm. The shaft 538 is machined from a LEXAN rod or equivalent material and has an outer diameter of about 2.2 cm and an inner diameter of about 16 mm.

The plunger head 550 has a concentric inner ring of seven holes 560 and an outer ring of 14 holes 554, all holes having a diameter of about 8.8 millimeters as well as a hole of about 16 mm aligned with the shaft. The plunger head 550 is machined from a LEXAN rod or equivalent material and has a height of approximately 16 mm and a diameter sized such that it fits within the cylinder 534 with minimum wall clearance but still slides freely. The total length of the plunger head 550 and shaft 538 is about 8.25 cm, but can be machined at the top of the shaft to obtain the desired mass of the plunger 536. The plunger 536 comprises a 100 mesh stainless steel cloth screen 564 that is biaxially stretched to tautness and attached to the lower end of the plunger 536. The screen is attached to the plunger head 550 using an appropriate solvent that causes the screen to be securely adhered to the plunger head 550. Care must be taken to avoid excess solvent migrating into the open portions of the screen and reducing the open area for liquid flow. Acrylic adhesive, Weld-On #4, from IPS Corporation (having a place of business in Gardena, Calif., USA) is a suitable adhesive.

The sample container 530 comprises a cylinder 534 and a 400 mesh stainless steel cloth screen 566 that is biaxially stretched to tautness and attached to the lower end of the cylinder 534. The screen is attached to the cylinder using an appropriate solvent that causes the screen to be securely adhered to the cylinder. Care must be taken to avoid excess solvent migrating into the open portions of the screen and reducing the open area for liquid flow. Acrylic adhesive, Weld-On #4, from IPS Corporation is a suitable adhesive. A gel particle sample, indicated as 568 in FIG. 2, is supported on the screen 566 within the cylinder 534 during testing.

The cylinder 534 may be bored from a transparent LEXAN rod or equivalent material, or it may be cut from a LEXAN tubing or equivalent material, and has an inner diameter of about 6 cm (e.g., a cross-sectional area of about 28.27 cm²), a wall thickness of about 0.5 cm and a height of approximately 7.95 cm. A step is machined into the outer diameter of the cylinder 534 such that a region 534a with an outer diameter of 66 mm exists for the bottom 31 mm of the cylinder 534. An o-ring 540 which fits the diameter of region 534a may be placed at the top of the step.

The annular weight 548 has a counter-bored hole about 2.2 cm in diameter and 1.3 cm deep so that it slips freely onto the shaft 538. The annular weight also has a thru-bore 548a of about 16 mm. The annular weight 548 can be made from stainless steel or from other suitable materials resistant to corrosion in the presence of the test solution, which is 0.9 weight percent sodium chloride solution in distilled water. The combined weight of the plunger 536 and annular weight 548 equals approximately 596 grams (g), which corresponds to a pressure applied to the sample 568 of about 0.3 pounds per square inch (psi), or about 20.7 dynes/cm² (2.07 kPa), over a sample area of about 28.27 cm².

When the test solution flows through the test apparatus during testing as described below, the sample container 530 generally rests on a weir 600. The purpose of the weir is to divert liquid that overflows the top of the sample container 530 and diverts the overflow liquid to a separate collection device 601. The weir can be positioned above a scale 602 with a beaker 603 resting on it to collect saline solution passing through the swollen sample 568.

To conduct the Gel Bed Permeability Test under "free swell" conditions, the plunger 536, with the weight 548 seated thereon, is placed in an empty sample container 530 and the height from the top of the weight 548 to the bottom of the sample container 530 is measured using a suitable gauge accurate to 0.01 mm. The force the thickness gauge applies during measurement should be as low as possible, preferably less than about 0.74 Newtons. It is important to measure the height of each empty sample container 530, plunger 536, and weight 548 combination and to keep track of which plunger 536 and weight 548 is used when using multiple test apparatus. The same plunger 536 and weight 548 should be used for measurement when the sample 568 is later swollen following saturation. It is also desirable that the base that the sample cup 530 is resting on is level, and the top surface of the weight 548 is parallel to the bottom surface of the sample cup 530.

The sample to be tested is prepared from the particulate superabsorbent polymer composition, which is prescreened through a U.S. standard 30 mesh screen and retained on a U.S. standard 50 mesh screen. As a result, the test sample comprises particles sized in the range of about 300 to about 600 microns. The superabsorbent polymer particles can be pre-screened with, for example, a RO-TAP Mechanical Sieve Shaker Model B available from W. S. Tyler, Inc., Mentor Ohio. Sieving is conducted for 10 minutes. Approximately 2.0 grams of the sample is placed in the sample container 530 and spread out evenly on the bottom of the sample container. The container, with 2.0 grams of sample in it, without the plunger 536 and weight 548 therein, is then submerged in the 0.9% saline solution for a time period of about 60 minutes to saturate the sample and allow the sample to swell free of any restraining load. During saturation, the sample cup 530 is set on a mesh located in the liquid reservoir so that the sample cup 530 is raised slightly above the bottom of the liquid reservoir. The mesh does not inhibit the flow of saline solution into the sample cup 530. A suitable mesh can be obtained as part number 7308 from Eagle Supply and Plastic, having a place of business in Appleton, Wis., U.S.A. Saline does not fully cover the superabsorbent polymer composition particles, as would be evidenced by a perfectly flat saline surface in the test cell. Also, saline depth is not allowed to fall so low that the surface within the cell is defined solely by swollen superabsorbent, rather than saline.

At the end of this period, the plunger 536 and weight 548 assembly is placed on the saturated sample 568 in the sample container 530 and then the sample container 530, plunger 536, weight 548, and sample 568 are removed from the solution. After removal and before being measured, the sample container 530, plunger 536, weight 548, and sample 568 are to remain at rest for about 30 seconds on a suitable flat, large grid non-deformable plate of uniform thickness. The thickness of the saturated sample 568 is determined by again measuring the height from the top of the weight 548 to the bottom of the sample container 530, using the same thickness gauge used previously provided that the zero point is unchanged from the initial height measurement. The sample container 530, plunger 536, weight 548, and sample 568 may be placed on a flat, large grid non-deformable plate of uniform thickness that will provide for drainage. The plate has an overall dimension of 7.6 cm by 7.6 cm, and each grid has a cell size dimension of 1.59 cm long by 1.59 cm wide by 1.12 cm deep. A suitable flat, large grid non-deformable plate material is a parabolic diffuser panel, catalogue number 1624K27, available from McMaster Carr Supply Company, having a place of business in Chicago, Ill., U.S.A., which can then be cut to the proper dimensions. This flat, large mesh non-deformable plate must also be present when measuring the height of the initial empty assembly. The height measurement should be made as soon as practicable after the thickness gauge is engaged. The height measurement obtained from measuring the empty sample container 530, plunger 536, and weight 548 is subtracted from the height measurement obtained after saturating the sample 568. The resulting value is the thickness, or height "H" of the swollen sample.

The permeability measurement is initiated by delivering a flow of the 0.9% saline solution into the sample container 530 with the saturated sample 568, plunger 536, and weight 548 inside. The flow rate of test solution into the container is adjusted to cause saline solution to overflow the top of the cylinder 534 thereby resulting in a consistent head pressure equal to the height of the sample container 530. The test solution may be added by any suitable means that is sufficient to ensure a small, but consistent amount of overflow from the top of the cylinder, such as with a metering pump 604. The overflow liquid is diverted into a separate collection device 601. The quantity of solution passing through the sample 568 versus time is measured gravimetrically using the scale 602 and beaker 603. Data points from the scale 602 are collected every second for at least sixty seconds once the overflow has begun. Data collection may be taken manually or with data collection software. The flow rate, Q, through the swollen sample 568 is determined in units of grams/second (g/s) by a linear least-square fit of fluid passing through the sample 568 (in grams) versus time (in seconds).

Permeability in cm² is obtained by the following equation:

$$K=[Q*H*\mu]/[A*\rho*P]$$

where K=Permeability (cm²), Q=flow rate (g/sec), H=height of swollen sample (cm), μ=liquid viscosity (poise) (approximately one centipoise for the test solution used with this Test), A=cross-sectional area for liquid flow (28.27 cm² for the sample container used with this Test), ρ=liquid density (g/cm³) (approximately one g/cm³, for the test solution used with this Test) and P=hydrostatic pressure (dynes/cm²) (normally approximately 7,797 dynes/cm²). The hydrostatic pressure is calculated from P=ρ*g*h, where ρ=liquid density (g/cm³), g=gravitational acceleration, nominally 981 cm/sec², and h=fluid height, e.g., 7.95 cm for the Gel Bed Permeability Test described herein.

A minimum of two samples is tested and the results are averaged to determine the gel bed permeability of the sample of particulate superabsorbent polymer composition.

The FSGBP can be measured as described herein prior to subjecting a particulate superabsorbent polymer composition to a Processing Test as described herein. Such a FSGBP value can be referred to as the "original" FSGBP of the particulate superabsorbent polymer composition. The FSGBP may also be measured subsequent to subjecting the particulate superabsorbent polymer composition to the Processing Test. Such a FSGBP value can be referred to as the "post processing" FSGBP. Comparing the original FSGBP of a particulate superabsorbent polymer composition with the post processing FSGBP of the particulate superabsorbent polymer composition can be used as a measure of the stability of the composition. It should be noted that all "original" and "post processing" FSGBP values reported herein were measured using a sample of pre-screened 300 to 600 µm particles.

Absorbency Under Load Test (AUL(0.9 Psi))

The Absorbency Under Load (AUL) Test measures the ability of the particulate superabsorbent polymer composition to absorb a 0.9 weight percent solution of sodium chloride in distilled water at room temperature (test solution) while the material is under a 0.9 psi load. The apparatus for testing AUL consists of:

An AUL assembly including a cylinder, a 4.4 g piston, and a standard 317 gm weight. The components of this assembly are described in additional detail below.

A flat-bottomed square plastic tray that is sufficiently broad to allow the glass fits to lay on the bottom without contact with the tray walls. A plastic tray that is 9" by 9" (22.9 cm×22.9 cm), with a depth of 0.5 to 1" (1.3 cm to 2.5 cm) is commonly used for this test method.

A 9 cm diameter sintered glass frit with a 'C' porosity (25-50 microns). This frit is prepared in advance through equilibration in saline (0.9% sodium chloride in distilled water, by weight). In addition to being washed with at least two portions of fresh saline, the frit must be immersed in saline for at least 12 hours prior to AUL measurements.

Whatman Grade 1, 9 cm diameter filter paper circles.

A supply of saline (0.9% sodium chloride in distilled water, by weight).

Figure 4:
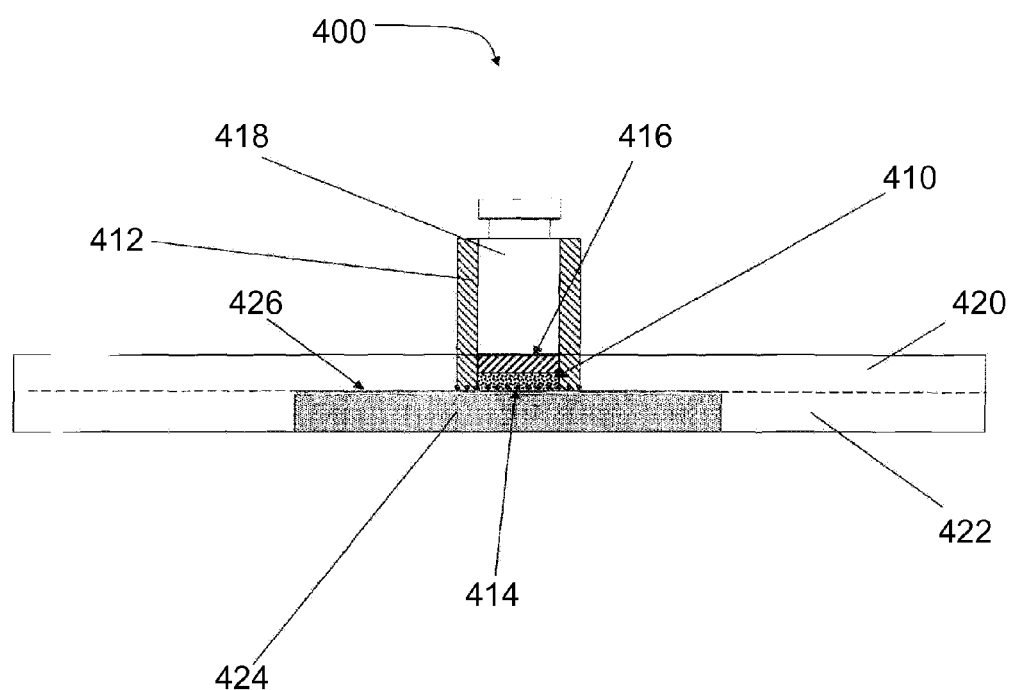
FIG. 4 is a side view of the test apparatus employed for the Absorbency Under Load Test.

Referring to FIG. 4, the cylinder 412 of the AUL assembly 400 used to contain the particulate superabsorbent polymer composition 410 is made from one-inch (2.54 cm) inside diameter thermoplastic tubing machined-out slightly to be sure of concentricity. After machining, a 400 mesh stainless steel wire cloth 414 is attached to the bottom of the cylinder 412 by heating the steel wire cloth 414 in a flame until red hot, after which the cylinder 412 is held onto the steel wire cloth until cooled. A soldering iron can be utilized to touch up the seal if unsuccessful or if it breaks. Care must be taken to maintain a flat smooth bottom and not distort the inside of the cylinder 412.

The 4.4 g piston (416) is made from one-inch diameter solid material (e.g., PLEXIGLAS®) and is machined to closely fit without binding in the cylinder 412.

A standard 317 gm weight 418 is used to provide a 62,053 dyne/cm² (about 0.9 psi) restraining load. The weight is a cylindrical, 1 inch (2.5 cm) diameter, stainless steel weight that is machined to closely fit without binding in the cylinder.

Unless specified otherwise, a sample 410 corresponding to a layer of at least about 300 gsm. (0.16 g) of superabsorbent polymer composition particles is utilized for testing the AUL. The sample 410 is taken from superabsorbent polymer composition particles that are pre-screened through U.S. standard #30 mesh and retained on U.S. std. #50 mesh. The superabsorbent polymer composition particles can be pre-screened with, for example, a RO-TAP® Mechanical Sieve Shaker Model B available from W. S. Tyler, Inc., Mentor Ohio. Sieving is conducted for about 10 minutes.

The inside of the cylinder 412 is wiped with an antistatic cloth prior to placing the superabsorbent polymer composition particles 410 into the cylinder 412.

The desired amount of the sample of sieved particulate superabsorbent polymer composition 410 (about 0.16 g) is weighed out on a weigh paper and evenly distributed on the wire cloth 414 at the bottom of the cylinder 412. The weight of the particulate superabsorbent polymer composition in the bottom of the cylinder is recorded as 'SA,' for use in the AUL calculation described below. Care is taken to be sure no particulate superabsorbent polymer composition cling to the wall of the cylinder. After carefully placing the 4.4 g piston 412 and 317 g weight 418 on the superabsorbent polymer composition particles 410 in the cylinder 412, the AUL assembly 400 including the cylinder, piston, weight, and particulate superabsorbent polymer composition particles is weighed, and the weight is recorded as weight 'A'.

A sintered glass frit 424 (described above) is placed in the plastic tray 420, with saline 422 added to a level equal to that of the upper surface of the glass frit 424. A single circle of filter paper 426 is placed gently on the glass frit 424, and the AUL assembly 400 with the particulate superabsorbent polymer composition 410 is then placed on top of the filter paper 426. The AUL assembly 400 is then allowed to remain on top of the filter paper 426 for a test period of one hour, with attention paid to keeping the saline level in the tray constant. At the end of the one hour test period, the AUL apparatus is then weighed, with this value recorded as weight 'B.'

The AUL(0.9 psi) is calculated as follows:

$$AUL(0.9 \text{ psi}) = (B-A)/SA$$

wherein
A=Weight of AUL Unit with dry SAP
B=Weight of AUL Unit with SAP after 60 minutes absorption
SA=Actual SAP weight A minimum of two tests is performed and the results are averaged to determine the AUL value under 0.9 psi load. The particulate superabsorbent polymer composition samples are tested at about 23° C. and about 50% relative humidity.

Absorbency Against Pressure [AAP(0.7 Psi)]

A stainless-steel 400-mesh standard sieve (mesh size of 38 µm) was fused on the bottom of a plastic support cylinder having an inner diameter of 60 mm, and 0.9000 g of water absorbent resin or water absorbent was uniformly sprinkled on the sieve. A piston with an outer diameter slightly smaller than 60 mm, sized to fit inside the support cylinder with no clearance but with a free vertical stroke within the cylinder was prepared. The piston was adjusted in such a manner that a load of 4.83 kPa (0.7 psi) could be uniformly applied on the water absorbent resin or water absorbent. The piston and the load were placed in this order on the water absorbent resin or water absorbent, and the total mass Wa (g) of this measuring device was measured. Then, a glass filter having a diameter of 90 mm (made by Sougo Rikagaku Garasu Seisakusho Co., Ltd.; pore diameter of 100 µm to 120 µm) was placed inside a Petri dish having a diameter of 150 mm, and each solution was added to the level of the upper surface of the glass filter.

On the glass filter, a piece of filter paper, Whatman Grade 1, 9 cm diameter filter paper circles was placed to completely wet the filter paper, and an excess solution was removed.

The measuring device was then placed on the wet filter paper to absorb the contacted solution under pressure. After 1 hour, the measuring device was lifted and a weight Wb (g) of the measuring device was measured. From the values of Wa and Wb so measured, an absorbency against pressure (g/g) was calculated using the following formula:

$$AAP(0.7)(g/g) = (Wb(g) - Wa(g))/(0.9 \text{ g of water absorbent resin})$$

Moisture Content Test

The amount of water content, measured as "% moisture," can be measured as follows: 1) Weigh 5.0 grams of superabsorbent polymer composition (SAP) accurately in a pre-weighed aluminum weighing pan; 2) place the SAP and pan into a standard lab oven preheated to 105° C. for 3 hours; 3) remove and re-weigh the pan and contents; and 4) calculate the percent moisture using the following formula:

$$\% \text{ Moisture} = \{((\text{pan wt} + \text{initial SAP wt}) - (\text{dried SAP \& pan wt}))*100\}/\text{initial SAP wt}$$

Compressibility Test

The compressibility test measures the relative volume change of the particulate superabsorbent polymer composition as a response to a pressure change. The test is conducted on a Zwick Tensile/Compression Tester Zwicki 1120. A sample of the superabsorbent polymer composition is placed in a testing cell of a thick-walled cylinder closed at the bottom and fitted at the top with a movable piston. The cylinder is 5 cm in diameter and 1 cm in depth. The piston moves at a speed of 0.2 mm/min. The normal force starts to increase when the piston touches the surface of the sample. The test is completed when the normal force reaches 90 N. The sample heights at the normal forces of 0N and 90N are recorded automatically by the computer that is hooked to the Zwick Tensile/Compression Tester.

$$\text{Compressibility} = (\text{initial height} - \text{final height})/(\text{initial height}) \times (\text{surface area of piston})/(\text{maximum normal force})$$

Processing Test

The processing test measures the stability of performance properties of the superabsorbent polymer composition against external forces. The test conditions are selected to simulate the debulking process of absorbent articles. 40 grams of a sample of a particulate superabsorbent polymer composition is distributed through an eight inch US standard 18 mesh screen onto a piece of chipboard (dimension 22.5"×17.25"×0.03", commercially available from Central Wisconsin Paper which is located in Wausau, Wis., USA) to form an eight inch diameter circle. Another piece of chipboard is then placed over the sample to form a chipboard-sample-chipboard sandwich. The sandwich is then put through a two roll calendar press (BF Perkins serial number H8617-67) set at 1150 pounds per square inch of hydraulic pressure and a speed of 20 rpm. The processed sample is then removed from the chipboard. The CRC, AUL and FSGBP are then determined for the original and processed samples. The permeability stability index is used as the indicator of the stability of the superabsorbent polymer composition. It is calculated as follows:

$$\text{Permeability Stability Index} = (\text{GBP of processed sample})/(\text{GBP of original sample}).$$

EXAMPLES

The following SAP Preproducts A, B and B1, Neutralized Aluminum Salts C—F, Comparative Examples 1-5, and Examples 1-14 are provided to illustrate the inventions of products including particulate superabsorbent polymer composition and processes to make particulate superabsorbent polymer composition as set forth in the claims, and do not limit the scope of the claims. Unless otherwise stated all parts, and percentages are based on the dry particulate superabsorbent polymer composition.

SAP Preproduct A

A superabsorbent polymer may be made in the following way. Into a polyethylene vessel equipped with an agitator and cooling coils was added, 2.0 kg of 50% NaOH and 3.32 kg of distilled water and cooled to 20° C. 0.8 kg of glacial acrylic acid was then added to the caustic solution and the solution again cooled to 20° C. 4.8 g of polyethylene glycol monoallylether acrylate, 4.8 g of ethoxylated trimethylol propane triacrylate SARTOMER® 454 product, and 1.6 kg of glacial acrylic acid were added to the first solution, followed by cooling to 4-6° C. Nitrogen was bubbled through the monomer solution for about 5 minutes. The monomer solution was then discharged into a rectangular tray. 80 g of 1% by weight of $H_2O_2$ aqueous solution, 120 g of 2 wt % aqueous sodium persulfate solution, and 72 g of 0.5 wt % aqueous sodium erythorbate solution was added into the monomer solution to initiate polymerization reaction. The agitator was stopped and the initiated monomer was allowed to polymerize for 20 minutes.

A particulate superabsorbent polymer may be prepared as follows. The resulting hydrogel was chopped and extruded with a Hobart 4M6 commercial extruder, followed by drying in a Procter & Schwartz Model 062 forced air oven at 175° C. for 12 minutes with up flow and 6 minutes with down flow air on a 20 inch×40 inch perforated metal tray to a final product moisture level of less than 5 wt %. The dried material was coarse-ground in a Prodeva Model 315-S crusher, milled in an MPI 666-F three-stage roller mill and sieved with a Minox MTS 600DS3V to remove particles greater than 850 μm and smaller than 150 μm. The obtained Preproduct A contained 4.0% of moisture.

SAP Preproduct B

A superabsorbent polymer may be made in the following way. Into a polyethylene vessel equipped with an agitator and cooling coils was added, 1.9 kg of 50% NaOH and 3.34 kg of distilled water and cooled to 20° C. 0.83 kg of glacial acrylic acid was then added to the caustic solution and the solution again cooled to 20° C. 4.46 g of polyethylene glycol monoallylether acrylate, 4.46 g of ethoxylated trimethylol propane triacrylate SARTOMER® 454 product, and 1.65 kg of glacial acrylic acid were added to the first solution, followed by cooling to 4-6° C. Nitrogen was bubbled through the monomer solution for about 5 minutes. The monomer solution was then discharged into a rectangular tray. 80 g of 1% by weight of $H_2O_2$ aqueous solution, 120 g of 2 wt % aqueous sodium persulfate solution, and 72 g of 0.5 wt % aqueous sodium erythorbate solution was added into the monomer solution to initiate polymerization reaction. The agitator was stopped and the initiated monomer was allowed to polymerize for 20 minutes.

A particulate superabsorbent polymer may be prepared as follows. The resulting hydrogel was chopped and extruded with a Hobart 4M6 commercial extruder, followed by drying in a Procter & Schwartz Model 062 forced air oven at 175° C. for 12 minutes with up flow and 6 minutes with down flow air on a 20 inch×40 inch perforated metal tray to a final product moisture level of less than 5 wt %. The dried material was coarse-ground in a Prodeva Model 315-S crusher, milled in an MPI 666-F three-stage roller mill and sieved with a Minox MTS 600DS3V to remove particles greater than 850 μm and smaller than 150 μm. The obtained Preproduct B contained 4.3% of moisture.

SAP Preproduct A1

A superabsorbent polymer may be made in the following way. Into a polyethylene vessel equipped with an agitator and cooling coils was added, 2.0 kg of 50% NaOH and 3.32 kg of distilled water and cooled to 20° C. 0.8 kg of glacial acrylic acid was then added to the caustic solution and the solution again cooled to 20° C. 4.8 g of polyethylene glycol monoallylether acrylate, 4.8 g of ethoxylated trimethylol propane triacrylate SARTOMER® 454 product, and 1.6 kg of glacial acrylic acid were added to the first solution, followed by cooling to 4-6° C. Nitrogen was bubbled through the monomer solution for about 5 minutes. The monomer solution was then discharged into a rectangular tray. 80 g of 1% by weight of $H_2O_2$ aqueous solution, 120 g of 2 wt % aqueous sodium persulfate solution, and 72 g of 0.5 wt % aqueous sodium erythorbate solution was added into the monomer solution to initiate polymerization reaction. The agitator was stopped and the initiated monomer was allowed to polymerize for 20 minutes.

A particulate superabsorbent polymer may be prepared as follows. The resulting hydrogel was chopped and extruded with a Hobart 4M6 commercial extruder, followed by drying in a Procter & Schwartz Model 062 forced air oven at 175° C. for 12 minutes with up flow and 6 minutes with down flow air on a 20 inch×40 inch perforated metal tray to a final product moisture level of less than 5 wt %. The dried material was coarse-ground in a Prodeva Model 315-S crusher, milled in an MPI 666-F three-stage roller mill and sieved with a Minox MTS 600DS3V to remove particles greater than 700 μm and smaller than 150 μm. The obtained Preproduct A1 contained 12% of particles larger than 600 μm. The moisture content of the obtained Preproduct A1 was measured as 4.0%.

Neutralized Aluminum Salt C 200 g of aluminum sulfate solution (20% aqueous solution) was stirred in a beaker with a magnetic stirring bar. To this solution was added sodium hydroxide solution (50% aqueous solution) until the pH of the mixture reached 7. Totally 130 g of sodium hydroxide solution was consumed. The white colloidal suspension was stirred for 15 minutes and further sheared with Turnax mixer for about 1 minute to break down clumps. The neutralized aluminum solution was used for SAP modification without further purification.

Neutralized Aluminum Salt D 120 g of aluminum sulfate solution (20% aqueous solution) was stirred in a beaker with a magnetic stirring bar. To this solution was added sodium aluminate solution (20% aqueous solution) until the pH of the mixture reached 6.5. Totally 60 g of sodium aluminate solution was consumed. The white colloidal suspension was stirred for 15 minutes and further sheared with Turnax mixer for about 1 minute to break down clumps. The neutralized aluminum solution was used for SAP modification without further purification.

Neutralized Aluminum Salt E

To a 1000-ml beaker were added 49 g of lactic acid (88%, commercially available from ADM) and 161.5 g of water. The beaker was cooled in an ice bath and the solution was stirred with a magnetic stirring bar. A solution of sodium aluminate (73.2 g, 43% wt/wt in water) was added into the beaker. Then a solution of aluminum sulfate hydrate (59.3 g, 48% wt/wt in water) was added into the beaker. The resulting mixture was a clear solution with a pH value of 6.3. The neutralized aluminum salt solution obtained was used for SAP surface modification.

Neutralized Aluminum Salt F

To a 1000-ml beaker were added 19.2 g of glycolic acid (commercially available from Sigma-Aldrich) and 130.1 g of water. The beaker was cooled in an ice bath and the solution was stirred with a magnetic stirring bar. A solution of sodium aluminate (103.7 g, 20% wt/wt in water) was added into the beaker. Then a solution of aluminum sulfate hydrate (44.9 g, 40% wt/wt in water) was added into the beaker. The resulting mixture was a clear solution with a pH value of 6.0. The neutralized aluminum salt solution obtained was used for SAP surface modification.

Comparative Example 1

4 g of aluminum sulfate hydrate solution (48% wt/wt in water) and 12 g of ethylene carbonate solution (33% wt/wt in water) were applied on the surface of 400 g of SAP preproduct A using a finely atomized spray from a Paasche VL sprayer while the SAP particles were fluidized in air and continuously mixed. The coated material was then heated in a convection oven at 185° C. for 55 minutes for surface crosslinking. The surface crosslinked particulate material was then sieved with 20/100 mesh US standard sieves to remove particles greater than 850 μm and smaller than 150 μm. The moisture content of the product obtained was measured as 0.1%. The average AAP(0.7 psi) of the product is 21.7.

Comparative Example 2

6 g of sodium aluminate solution (33% wt/wt in water) and 12 g of ethylene carbonate solution (33% wt/wt in water) were applied on the surface of 400 g of SAP preproduct A using a finely atomized spray from a Paasche VL sprayer while the SAP particles were fluidized in air and continuously mixed. The coated material was then heated in a convection oven at 185° C. for 55 minutes for surface crosslinking. The surface crosslinked particulate material was then sieved with 20/100 mesh US standard sieves to remove particles greater than 850 μm and smaller than 150 μm. The moisture content of the product obtained was measured as 0.2%. The average AAP(0.7 psi) of the product is 20.7.

Comparative Example 3

16 g of neutralized aluminum salt solution C and 8 g of ethylene carbonate solution (50% wt/wt in water) were applied on the surface of 400 g of SAP preproduct A using a finely atomized spray from a Paasche VL sprayer while the SAP particles were fluidized in air and continuously mixed. The coated material was then heated in a convection oven at 185° C. for 55 minutes for surface crosslinking. The surface crosslinked particulate material was then sieved with 20/100 mesh US standard sieves to remove particles greater than 850 μm and smaller than 150 μm. The moisture content of the product obtained was measured as 0.13%. The average AAP (0.7 psi) of the product is 20.1.

Comparative Example 4

11.4 g of neutralized aluminum salt solution E was mixed with 12 g of ethylene carbonate solution (33% wt/wt in water). The mixture was applied on the surface of 400 g of SAP preproduct A using a finely atomized spray from a Paasche VL sprayer while the SAP particles were fluidized in air and continuously mixed. The coated material was then heated in a convection oven at 185° C. for 55 minutes for surface crosslinking. The surface crosslinked particulate material was then sieved with 20/100 mesh US standard sieves to remove particles greater than 850 μm and smaller than 150 μm. The moisture content of the product obtained was measured as 0.2%. The average AAP(0.7 psi) of the product is 19.7.

Comparative Example 5

11.4 g of neutralized aluminum salt solution E was mixed with 12 g of ethylene carbonate solution (33% wt/wt in water). The mixture was applied on the surface of 400 g of SAP preproduct A using a finely atomized spray from a Paasche VL sprayer while the SAP particles were fluidized in air and continuously mixed. The coated material was then heated in a convection oven at 185° C. for 55 minutes for surface crosslinking. The surface crosslinked particulate material was cooled down to below 60° C. 11.4 g of neutralized aluminum salt solution E, 0.4 g of polyethylene glycol (molecular weight 8000), and 8.0 g of deionized water were mixed to give a clear solution. The resulting mixture was applied on the surface crosslinked particulate material using a finely atomized spray from a Paasche VL sprayer while the SAP particles were fluidized in air and continuously mixed. The coated material was relaxed at room temperature for one day and then sieved with 20/100 mesh US standard sieves to remove particles greater than 850 μm and smaller than 150 μm. The moisture content of the product obtained was measured as 2.3%. The average AAP(0.7 psi) of the product is 21.7.

Example 1

16 g of neutralized aluminum salt solution C and 8 g of ethylene carbonate solution (50% wt/wt in water) were applied on the surface of 400 g of SAP preproduct A using a finely atomized spray from a Paasche VL sprayer while the SAP particles were fluidized in air and continuously mixed. The coated material was then heated in a convection oven at 185° C. for 55 minutes for surface crosslinking. The surface crosslinked particulate material was then sieved with 20/100 mesh US standard sieves to remove particles greater than 850 μm and smaller than 150 μm. The moisture content of the product obtained was measured as 0.13%. The surface crosslinked particulate material was cooled down to below 60° C. and coated with a solution containing 0.4 g of polyethylene glycol (molecular weight 8000) and 40 g of deionized water. The coated material was relaxed at room temperature for one day and then sieved with 20/100 mesh US standard sieves to remove particles greater than 850 μm and smaller than 150 μm. The moisture content of the product obtained was measured as 7.9%. The average AAP(0.7 psi) of the product is 18.8.

Example 2

16 g of neutralized aluminum salt solution C and 8 g of ethylene carbonate solution (50% wt/wt in water) were applied on the surface of 400 g of SAP preproduct A using a finely atomized spray from a Paasche VL sprayer while the SAP particles were fluidized in air and continuously mixed. The coated material was then heated in a convection oven at 185° C. for 55 minutes for surface crosslinking. The surface crosslinked particulate material was then sieved with 20/100 mesh US standard sieves to remove particles greater than 850 μm and smaller than 150 μm. The moisture content of the product obtained was measured as 0.13%. The surface crosslinked particulate material was cooled down to below 60° C. and coated with a solution containing 0.4 g of polyethylene glycol (molecular weight 8000), 1.6 g of sodium lactate and 40 g of deionized water. The coated material was relaxed at room temperature for one day and then sieved with 20/100 mesh US standard sieves to remove particles greater than 850 μm and smaller than 150 μm. The moisture content of the product obtained was measured as 7.9%. The average AAP(0.7 psi) of the product is 18.9.

Example 3

16 g of neutralized aluminum salt solution C and 8 g of ethylene carbonate solution (50% wt/wt in water) were applied on the surface of 400 g of SAP preproduct A using a finely atomized spray from a Paasche VL sprayer while the SAP particles were fluidized in air and continuously mixed. The coated material was then heated in a convection oven at 185° C. for 55 minutes for surface crosslinking. The surface crosslinked particulate material was then sieved with 20/100 mesh US standard sieves to remove particles greater than 850 μm and smaller than 150 μm. The moisture content of the product obtained was measured as 0.13%. The surface crosslinked particulate material was cooled down to below 60° C. and coated with a solution containing 0.4 g of polyethylene glycol (molecular weight 8000), 1.6 g of sodium gluconate and 40 g of deionized water. The coated material was relaxed at room temperature for one day and then sieved with 20/100 mesh US standard sieves to remove particles greater than 850 μm and smaller than 150 μm. The moisture content of the product obtained was measured as 7.8%. The average AAP(0.7 psi) of the product is 18.9.

Example 4

16 g of neutralized aluminum salt solution D and 8 g of ethylene carbonate solution (50% wt/wt in water) were applied on the surface of 400 g of SAP preproduct A using a finely atomized spray from a Paasche VL sprayer while the SAP particles were fluidized in air and continuously mixed. The coated material was then heated in a convection oven at 185° C. for 55 minutes for surface crosslinking. The surface crosslinked particulate material was then sieved with 20/100 mesh US standard sieves to remove particles greater than 850 μm and smaller than 150 μm. The moisture content of the product obtained was measured as 0.13%. The surface crosslinked particulate material was cooled down to below 60° C. and coated with a solution containing 0.4 g of polyethylene glycol (molecular weight 8000) and 40 g of deionized water. The coated material was relaxed at room temperature for one day and then sieved with 20/100 mesh US standard sieves to remove particles greater than 850 μm and smaller than 150 μm. The moisture content of the product obtained was measured as 7.5%. The average AAP(0.7 psi) of the product is 18.7.

Example 5

16 g of neutralized aluminum salt solution D and 8 g of ethylene carbonate solution (50% wt/wt in water) were applied on the surface of 400 g of SAP preproduct A using a finely atomized spray from a Paasche VL sprayer while the SAP particles were fluidized in air and continuously mixed. The coated material was then heated in a convection oven at 185° C. for 55 minutes for surface crosslinking. The surface crosslinked particulate material was then sieved with 20/100 mesh US standard sieves to remove particles greater than 850

μm and smaller than 150 μm. The moisture content of the product obtained was measured as 0.13%. The surface crosslinked particulate material was cooled down to below 60° C. and coated with a solution containing 0.4 g of polyethylene glycol (molecular weight 8000), 1.6 g of sodium lactate and 40 g of deionized water. The coated material was relaxed at room temperature for one day and then sieved with 20/100 mesh US standard sieves to remove particles greater than 850 μm and smaller than 150 μm. The moisture content of the product obtained was measured as 7.6%. The average AAP(0.7 psi) of the product is 18.6.

Example 6

16 g of neutralized aluminum salt solution D and 8 g of ethylene carbonate solution (50% wt/wt in water) were applied on the surface of 400 g of SAP preproduct A using a finely atomized spray from a Paasche VL sprayer while the SAP particles were fluidized in air and continuously mixed. The coated material was then heated in a convection oven at 185° C. for 55 minutes for surface crosslinking. The surface crosslinked particulate material was then sieved with 20/100 mesh US standard sieves to remove particles greater than 850 μm and smaller than 150 μm. The moisture content of the product obtained was measured as 0.13%. The surface crosslinked particulate material was cooled down to below 60° C. and coated with a solution containing 0.4 g of polyethylene glycol (molecular weight 8000), 1.6 g of sodium gluconate and 40 g of deionized water. The coated material was relaxed at room temperature for one day and then sieved with 20/100 mesh US standard sieves to remove particles greater than 850 μm and smaller than 150 μm. The moisture content of the product obtained was measured as 7.8%. The average AAP(0.7 psi) of the product is 18.2.

Example 7

11.4 g of neutralized aluminum salt solution E was mixed with 12 g of ethylene carbonate solution (33% wt/wt in water). The mixture was applied on the surface of 400 g of SAP preproduct A using a finely atomized spray from a Paasche VL sprayer while the SAP particles were fluidized in air and continuously mixed. The coated material was then heated in a convection oven at 185° C. for 55 minutes for surface crosslinking. The surface crosslinked particulate material was cooled down to below 60° C. 11.4 g of neutralized aluminum salt solution E, 0.4 g of polyethylene glycol (molecular weight 8000), and 28.0 g of deionized water were mixed to give a clear solution. The resulting mixture was applied on the surface crosslinked particulate material using a finely atomized spray from a Paasche VL sprayer while the SAP particles were fluidized in air and continuously mixed. The coated material was relaxed at room temperature for one day and then sieved with 20/100 mesh US standard sieves to remove particles greater than 850 μm and smaller than 150 μm. The product obtained contained 33% of particles larger than 600 μm. The moisture content of the product was measured as 7.1%. The average AAP(0.7 psi) of the product is 19.7.

Example 8

Same as Example 9 except the sieves were changed to 25/100 mesh US standard sieves. The product obtained contained 12% of particles larger than 600 μm. The moisture content of the product was measured as 7.5%. The average AAP(0.7 psi) of the product is 19.0.

Example 9

11.4 g of neutralized aluminum salt solution E was mixed with 12 g of ethylene carbonate solution (33% wt/wt in water). The mixture was applied on the surface of 400 g of SAP preproduct B using a finely atomized spray from a Paasche VL sprayer while the SAP particles were fluidized in air and continuously mixed. The coated material was then heated in a convection oven at 185° C. for 30 minutes for surface crosslinking. The surface crosslinked particulate material was cooled down to below 60° C. 11.4 g of neutralized aluminum salt solution E, 0.4 g of polyethylene glycol (molecular weight 8000), and 28.0 g of deionized water were mixed to give a clear solution. The resulting mixture was applied on the surface crosslinked particulate material using a finely atomized spray from a Paasche VL sprayer while the SAP particles were fluidized in air and continuously mixed. The coated material was relaxed at room temperature for one day and then sieved with 20/100 mesh US standard sieves to remove particles greater than 850 μm and smaller than 150 μm. The product obtained contained 25% of particles larger than 600 μm. The moisture content of the product was measured as 7.7%. The average AAP(0.7 psi) of the product is 20.3.

Example 10

11.4 g of neutralized aluminum salt solution E was mixed with 12 g of ethylene carbonate solution (33% wt/wt in water). The mixture was applied on the surface of 400 g of SAP preproduct A using a finely atomized spray from a Paasche VL sprayer while the SAP particles were fluidized in air and continuously mixed. The coated material was then heated in a convection oven at 185° C. for 55 minutes for surface crosslinking. The surface crosslinked particulate material was cooled down to below 60° C. 11.4 g of neutralized aluminum salt solution E, 0.4 g of polyethylene glycol (molecular weight 8000), and 40.0 g of deionized water were mixed to give a clear solution. The resulting mixture was applied on the surface crosslinked particulate material using a finely atomized spray from a Paasche VL sprayer while the SAP particles were fluidized in air and continuously mixed. The coated material was relaxed at room temperature for one day and then sieved with 20/100 mesh US standard sieves to remove particles greater than 850 μm and smaller than 150 μm. The moisture content of the product was measured as 11%. The average AAP(0.7 psi) of the product is 19.6.

Example 11

4 g of ethylene carbonate was dissolved in 19.7 g of neutralized aluminum salt solution F and the mixture was applied on the surface of 400 g of SAP preproduct A using a finely atomized spray from a Paasche VL sprayer while the SAP particles were fluidized in air and continuously mixed. The coated material was then heated in a convection oven at 185° C. for 55 minutes for surface crosslinking. The surface crosslinked particulate material was cooled down to below 60° C. 12 g of neutralized aluminum salt solution F, 0.4 g of polyethylene glycol (molecular weight 8000), and 32.0 g of deionized water were mixed to give a clear solution. The resulting mixture was applied on the surface crosslinked particulate material using a finely atomized spray from a Paasche VL sprayer while the SAP particles were fluidized in air and continuously mixed. The coated material was relaxed at room temperature for one day and then sieved with 20/100 mesh US standard sieves to remove particles greater than 850 μm and smaller than 150 μm. The moisture content of the product was measured as 8.5%. The average AAP(0.7 psi) of the product is 19.0.

Example 12

16 g of ethylene carbonate solution (25% wt/wt in water) was applied on the surface of 400 g of SAP preproduct A using a finely atomized spray from a Paasche VL sprayer while the SAP particles were fluidized in air and continuously mixed. The coated material was then heated in a convection oven at 185° C. for 55 minutes for surface crosslinking. The surface crosslinked particulate material was cooled down to below 60° C. 11.4 g of neutralized aluminum salt solution E, 0.4 g of polyethylene glycol (molecular weight 8000), and 24.0 g of deionized water were mixed to give a clear solution. The resulting mixture was applied on the surface crosslinked particulate material using a finely atomized spray from a Paasche VL sprayer while the SAP particles were fluidized in air and continuously mixed. The coated material was relaxed at room temperature for one day and then sieved with 20/100 mesh US standard sieves to remove particles greater than 850 μm and smaller than 150 μm. The product obtained contained 25% of particles larger than 600 μm. The moisture content of the product was measured as 7.7%. The average AAP(0.7 psi) of the product is 18.5.

Example 13

Same as Example 12 except that neutralized aluminum salt solution F was used instead of E. The moisture content of the product obtained was measured as 6%. The average AAP(0.7 psi) of the product is 19.3.

water). The mixture was applied on the surface of 400 g of SAP preproduct A1 using a finely atomized spray from a Paasche VL sprayer while the SAP particles were fluidized in air and continuously mixed. The coated material was then heated in a convection oven at 185° C. for 45 minutes for surface crosslinking. The surface crosslinked particulate material was cooled down to below 60° C. 11.4 g of neutralized aluminum salt solution E, 0.4 g of polyethylene glycol (molecular weight 8000), and 28.0 g of deionized water were mixed to give a clear solution. The resulting mixture was applied on the surface crosslinked particulate material using a finely atomized spray from a Paasche VL sprayer while the SAP particles were fluidized in air and continuously mixed. The coated material was relaxed at room temperature for one day and then sieved with 20/100 mesh US standard sieves to remove particles greater than 850 μm and smaller than 150 μm. The product obtained contained 7.9% of particles larger than 600 μm and had a mean PSD of 398 μm. The moisture content of the product was measured as 7.0%. Properties of the product included a CRC of 30.2 g/g, AUL(0.9 psi) of 17.8 g/g, AAP(0.7 psi) of 18.9 g/g, and a GBP of $46.2 \times 10^{-8}$ cm$^2$.

Notwithstanding that the numerical ranges and parameters setting forth the broad scope of the invention are approximations, the numerical values set forth in the specific examples are reported as precisely as possible. Other than in the operating examples, or where otherwise indicated, all numbers expressing quantities of ingredients, reaction conditions, and so forth used in the specification and claims are to be understood as being modified in all instances by the term "about." Any numerical value, however, inherently contain certain errors necessarily resulting from the standard deviation found in their respective testing measurements.

The invention claimed is:
1. A particulate superabsorbent polymer composition comprising a particulate superabsorbent polymer and from 0.01

TABLE 1

| Particulate superabsorbent polymer composition | Al Salt | pH of Al salt solution | CRC (g/g) | 0.9 AUL (g/g) | GBP ($\times 10^{-8}$ cm$^2$) | CRC after processing (g/g) | 0.9 AUL after processing (g/g) | GBP after processing ($\times 10^{-8}$ cm$^2$) | Permeability stability index | Compressibility (cm$^2$/N) |
|---|---|---|---|---|---|---|---|---|---|---|
| Comparative Example 1 | Al$_2$(SO$_4$)$_3$ | 2.8 | 32.2 | 20.2 | 14 | 35.5 | 13.9 | 3 | 0.19 | n.d. |
| Comparative Example 2 | NaAlO2 | 14 | 31.8 | 19.6 | 5 | 35.3 | 12.2 | 0.9 | 0.17 | n.d. |
| Comparative Example 3 | C | 7 | 32.6 | 17.9 | 31 | 35.2 | 13.5 | 8 | 0.28 | 1.0 |
| Comparative Example 4 | E | 6.3 | 30.7 | 18.7 | 54 | 31 | 16 | 11 | 0.20 | 0.8 |
| Comparative Example 5 | E | 6.3 | 29.8 | 19 | 68 | 30.3 | 18.5 | 32 | 0.47 | 1.15 |
| Example 1 | C | 7 | 29.2 | 16.3 | 23 | 29.5 | 16.1 | 19 | 0.81 | 1.8 |
| Example 2 | C | 7 | 28.7 | 16.7 | 26 | 29.3 | 16.2 | 18 | 0.70 | 1.7 |
| Example 3 | C | 7 | 28.6 | 17.2 | 24 | 29.6 | 16.2 | 19 | 0.78 | 1.4 |
| Example 4 | D | 6.5 | 29.5 | 16 | 40 | 30.1 | 15.7 | 32 | 0.81 | 1.5 |
| Example 5 | D | 6.5 | 28.8 | 16 | 42 | 29.8 | 15.4 | 30 | 0.73 | 1.7 |
| Example 6 | D | 6.5 | 28.6 | 16.2 | 41 | 30.0 | 14.9 | 29 | 0.71 | 3.2 |
| Example 7 | E | 6.3 | 28.7 | 19.5 | 65 | 28.6 | 18.8 | 53 | 0.81 | 1.5 |
| Example 8 | E | 6.3 | 28.8 | 19.4 | 68 | 29.1 | 19.2 | 58 | 0.85 | 1.3 |
| Example 9 | E | 6.3 | 31.5 | 19 | 55 | 31.4 | 16.6 | 43 | 0.78 | 1.4 |
| Example 10 | E | 6.3 | 28.2 | 17.5 | 66 | 27.8 | 16.8 | 61 | 0.93 | 1.5 |
| Example 11 | F | 6 | 28.8 | 17.3 | 53 | 30.2 | 16.1 | 50 | 0.95 | 1.8 |
| Example 12 | E | 6.3 | 30.9 | 18.3 | 32 | 31.3 | 16.2 | 23 | 0.72 | 1.4 |
| Example 13 | F | 6 | 29.6 | 16.9 | 50 | 29.8 | 16.1 | 37 | 0.74 | 1.4 |

Example 14

11.4 g of neutralized aluminum salt solution E was mixed with 12 g of ethylene carbonate solution (33% wt/wt in wt % to about 5 wt % based on the particulate superabsorbent polymer composition weight of a neutralized aluminum salt applied to the surface of the particulate superabsorbent polymer, in the form of an aqueous neutralized aluminum salt solution having a pH value from about 5.5 to about 8; wherein the particulate superabsorbent polymer composition has a Centrifuge Retention Capacity (CRC) of from about 25 grams to about 40 grams of 0.9 weight percent sodium chloride aqueous per gram of the particulate superabsorbent polymer composition, wherein the CRC is measured either before or after subjecting the superabsorbent polymer composition to a Processing Test, and an original Free Swell Gel Bed Permeability (FSGBP) of from about $20 \times 10^{-8}$ cm$^2$ to about $200 \times 10^{-8}$ cm$^2$ prior to subjecting the particulate superabsorbent polymer composition to the Processing Test; and a compressibility of from about 1.30 mm$^2$/N to 4 mm$^2$/N, and has a permeability stability index of from 0.60 to about 0.99 when subjecting the particulate superabsorbent polymer composition to a Processing Test, and having particles having a particle diameter of larger than 600 μm in an amount of from about 12 wt % to about 25 wt % of the particulate superabsorbent polymer composition and as specified by standard sieve classification.

2. The particulate superabsorbent polymer composition according to claim 1 wherein said particulate superabsorbent polymer composition having particles having a particle diameter of smaller than 600 μm and larger than 150 μm in an amount of not less than about 85 wt % of the particulate superabsorbent polymer composition and as specified by standard sieve classification and the particles having a weight average particle diameter (D50) specified by standard sieve classification of from 300 to 400 μm.

3. The particulate superabsorbent polymer composition according to claim 1 wherein said particulate superabsorbent polymer composition has a permeability stability index of from 0.70 to about 0.99.

4. The particulate superabsorbent polymer composition according to claim 1 wherein said aqueous neutralized aluminum salt solution has a pH value from about 6 to about 7.

5. The particulate superabsorbent polymer composition according to claim 1 wherein said neutralized aluminum salt is selected from:
   a) the reaction product of sodium hydroxide with aluminum sulfate or aluminum sulfate hydrate;
   b) the reaction product of an organic acid and sodium aluminate;
   c) the reaction product of sodium aluminate and aluminum sulfate or aluminum sulfate hydrate; or
   d) the reaction product of an organic acid or its salt and sodium aluminate and aluminum sulfate or aluminum sulfate hydrate.

6. A particulate superabsorbent polymer composition comprising a particulate superabsorbent polymer and from 0.01 wt % to about 5 wt % based on the particulate superabsorbent polymer composition weight of a neutralized aluminum salt applied to the surface of the particulate superabsorbent polymer, in the form of an aqueous neutralized aluminum salt solution having a pH value from about 5.5 to about 8; wherein the particulate superabsorbent polymer composition has a Centrifuge Retention Capacity (CRC) of from about 25 grams to about 40 grams of 0.9 weight percent sodium chloride aqueous per gram of the particulate superabsorbent polymer composition, wherein the CRC is measured either before or after subjecting the superabsorbent polymer composition to a Processing Test, and an original Free Swell Gel Bed Permeability (FSGBP) of from about $20 \times 10^{-8}$ cm$^2$ to about $200 \times 10^{-8}$ cm$^2$ prior to subjecting the particulate superabsorbent polymer composition to the Processing Test; and a compressibility of from about 1.30 mm$^2$/N to 4 mm$^2$/N and has a permeability stability index of from 0.60 to about 0.99 when subjecting the particulate superabsorbent polymer composition to a Processing Test, and having particles having a particle diameter of larger than 600 μm in an amount of less than about 15 wt % of the particulate superabsorbent polymer composition and as specified by standard sieve classification.

7. The particulate superabsorbent polymer composition according to claim 6 wherein said particulate superabsorbent polymer composition having particles having a particle diameter of smaller than 600 μm and larger than 150 μm in an amount of not less than about 85 wt % of the particulate superabsorbent polymer composition and as specified by standard sieve classification and the particles having a weight average particle diameter (D50) specified by standard sieve classification of from 300 to 400 μm.

8. The particulate superabsorbent polymer composition according to claim 6 wherein said particulate superabsorbent polymer composition having a particle diameter of larger than 600 μm in an amount of from about 6 wt % to about 15 wt % of the particulate superabsorbent polymer composition and as specified by standard sieve classification.

9. The particulate superabsorbent polymer composition according to claim 6 wherein said particulate superabsorbent polymer composition has a permeability stability index of from 0.70 to about 0.99.

10. The particulate superabsorbent polymer composition according to claim 6 wherein said aqueous neutralized aluminum salt solution has a pH value from about 6 to about 7.

11. The particulate superabsorbent polymer composition according to claim 6 wherein said neutralized aluminum salt is selected from:
    a) the reaction product of sodium hydroxide with aluminum sulfate or aluminum sulfate hydrate;
    b) the reaction product of an organic acid and sodium aluminate;
    c) the reaction product of sodium aluminate and aluminum sulfate or aluminum sulfate hydrate; or
    d) the reaction product of an organic acid or its salt and sodium aluminate and aluminum sulfate or aluminum sulfate hydrate.

12. A particulate superabsorbent polymer composition comprising:
    a) from about 55 wt % to about 85 wt % of polymerizable unsaturated acid group containing monomers selected from acrylic acid, methacrylic acid, or 2-acrylamido-2-methylpropanesulfonic acid, or mixtures thereof;
    b) from about 14 wt % to about 45 wt % of an alkali base selected from sodium hydroxide or potassium hydroxide to neutralize the polymerizable unsaturated acid group containing monomers of a) to from about 50 to about 80 mol %;
    c) from about 0.001 wt % to about 5.0 wt % based on the weight of a) of an internal crosslinking agent, wherein the components a), b) and c) are polymerized into a hydrogel which is granulated into particulate superabsorbent polymer having a surface;
    d) from about 0.001 wt % to about 5.0 wt % based on the particulate superabsorbent composition weight of surface crosslinking agent applied to the surface of the particulate superabsorbent polymer;
    e) from 0.001 wt to about 5.0 wt % based on the particulate superabsorbent composition weight of a neutralized aluminum salt applied to the surface of the particulate superabsorbent polymer, in the form of an aqueous neutralized aluminum salt solution having a pH value from about 5.5 to about 8;
    wherein the particulate superabsorbent polymer composition has a Centrifuge Retention Capacity of from about 25 grams to about 40 grams of 0.9 weight percent sodium chloride aqueous per gram of the particulate superabsorbent polymer composition, wherein the CRC is measured either before or after subjecting the particulate superabsorbent polymer composition to a Processing Test, and an original Free Swell Gel Bed Permeability (FSGBP) of about $20\times10^{-8}$ cm$^2$ to about $200\times10^{-8}$ cm$^2$ prior to subjecting the particulate superabsorbent polymer composition to the Processing Test; and has a permeability stability index of from 0.60 to about 0.99, and a compressibility of from 1.30 mm$^2$/N to about 4 mm$^2$/N, and from 0 to about 12 wt % of particles larger than about 600 μm specified by standard sieve classification and the particles having a weight average particle diameter (D50) specified by standard sieve classification of from 300 to 400 μm.

13. The particulate superabsorbent polymer composition according to claim 12 wherein said aqueous neutralized aluminum salt solution has a pH value from about 6 to about 7.

14. The particulate superabsorbent polymer composition according to claim 13 wherein said particulate superabsorbent polymer composition having a particle diameter of larger than 600 μm in an amount of from about 3 wt % to about 12 wt % of the particulate superabsorbent polymer composition and as specified by standard sieve classification.

15. The particulate superabsorbent polymer composition according to claim 13 wherein said neutralized aluminum salt is selected from:
   a) the reaction product of sodium hydroxide with aluminum sulfate or aluminum sulfate hydrate;
   b) the reaction product of an organic acid with sodium aluminate;
   c) the reaction product of sodium aluminate with aluminum sulfate or aluminum sulfate hydrate; or
   d) the reaction product of an organic acid or its salt with sodium aluminate and aluminum sulfate or aluminum sulfate hydrate.

16. The particulate superabsorbent polymer composition according to claim 12 having a moisture content of about 6 wt % to about 15 wt % based on the particulate superabsorbent polymer composition.

17. The particulate superabsorbent polymer composition according to claim 14 said organic acid is selected from glycolic acid, lactic acid or gluconic acid.

18. A process for the production of a particulate superabsorbent polymer composition according to claim 1 comprising the following steps:
   a) providing a particulate superabsorbent polymer;
   b) preparing a neutralized aluminum salt in the form of an aqueous solution having a pH value from about 5.5 to about 8; and;
   c) applying the aqueous neutralized aluminum salt solution on the surface of the particulate superabsorbent polymer; and
   wherein the particulate superabsorbent polymer composition has a degree of neutralization of from about 50 mol % to about 80 mol %; and the particulate superabsorbent polymer composition has a Centrifuge Retention Capacity of from about 25 grams to about 40 grams of 0.9 weight percent sodium chloride aqueous per gram of the particulate superabsorbent polymer composition, wherein the CRC is measured either before or after subjecting the superabsorbent polymer composition to a Processing Test, and a Free Swell Gel Bed Permeability (FSGBP) of about $20\times10^{-8}$ cm$^2$ to about $200\times10^{-8}$ cm$^2$ prior to subjecting the treated particulate superabsorbent polymer composition to the Processing Test; and a compressibility from 1.30 mm$^2$/N to about 4 mm$^2$/N, a permeability stability index of from 0.60 to about 0.99 when subjecting the particulate superabsorbent polymer composition to a Processing Test, and the particles having a weight average particle diameter (D50) specified by standard sieve classification of from 300 to 400 μm.

19. The process according to claim 18 wherein said aqueous aluminum salt solution has a pH value from about 6 to about 7.

20. The process according to claim 18 wherein particles have a particle diameter of smaller than 600 μm and not smaller than 150 μm in an amount of not less than about 90 wt % of the particulate superabsorbent polymer composition.

21. The process according to claim 18 wherein said neutralized aluminum salt is selected from:
   a) the reaction product of sodium hydroxide with aluminum sulfate or aluminum sulfate hydrate;
   b) the reaction product of an organic acid with sodium aluminate;
   c) the reaction product of sodium aluminate with aluminum sulfate or aluminum sulfate hydrate; or
   d) the reaction product of an organic acid or its salt with sodium aluminate and aluminum sulfate or aluminum sulfate hydrate.

* * * * *